United States Patent
Madsen et al.

(10) Patent No.: US 10,794,916 B2
(45) Date of Patent: Oct. 6, 2020

(54) METHODS OF GLYCOPROTEIN ANALYSIS

(71) Applicant: Momenta Pharmaceuticals, Inc., Cambridge, MA (US)

(72) Inventors: James Madsen, Medford, MA (US); James Anderson, Hudson, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 197 days.

(21) Appl. No.: 15/571,696

(22) PCT Filed: May 5, 2016

(86) PCT No.: PCT/US2016/030994
§ 371 (c)(1),
(2) Date: Nov. 3, 2017

(87) PCT Pub. No.: WO2016/179397
PCT Pub. Date: Nov. 10, 2016

(65) Prior Publication Data
US 2018/0149661 A1 May 31, 2018

Related U.S. Application Data

(60) Provisional application No. 62/220,081, filed on Sep. 17, 2015, provisional application No. 62/157,926, filed on May 6, 2015.

(51) Int. Cl.
*G01N 33/68* (2006.01)
*G01N 30/72* (2006.01)
*C07K 16/00* (2006.01)
*G01N 30/88* (2006.01)
*H01J 49/00* (2006.01)

(52) U.S. Cl.
CPC ......... *G01N 33/6848* (2013.01); *C07K 16/00* (2013.01); *G01N 30/7233* (2013.01); *G01N 30/88* (2013.01); *H01J 49/004* (2013.01); *C07K 2317/10* (2013.01); *C07K 2317/40* (2013.01); *C07K 2317/41* (2013.01); *C07K 2317/52* (2013.01); *C07K 2317/524* (2013.01); *C07K 2317/526* (2013.01); *C07K 2319/30* (2013.01); *G01N 2030/8831* (2013.01); *G01N 2560/00* (2013.01)

(58) Field of Classification Search
CPC ........... G01N 33/6848; G01N 2560/00; G01N 2030/8831; C07K 2317/10
See application file for complete search history.

(56) References Cited

U.S. PATENT DOCUMENTS

| | | | |
|---|---|---|---|
| 6,003,666 | A | 12/1999 | Dougherty |
| 7,329,353 | B2 | 2/2008 | Dillon et al. |
| 2006/0275282 | A1 | 12/2006 | Moore et al. |
| 2007/0059685 | A1 | 3/2007 | Kohne |
| 2012/0264155 | A1 | 10/2012 | Frandsen et al. |
| 2014/0080218 | A1 | 3/2014 | Shriver et al. |
| 2014/0356968 | A1 | 12/2014 | Niazi |
| 2019/0079100 | A1 | 3/2019 | Tsao et al. |

FOREIGN PATENT DOCUMENTS

| | | |
|---|---|---|
| WO | WO-2013/181576 A2 | 12/2013 |
| WO | WO-2013/181585 A2 | 12/2013 |
| WO | WO-2016/179535 A1 | 11/2016 |

OTHER PUBLICATIONS

Huang, Richard. Y.C. et al. "Higher order structure characterization of protein therapeutics by hydrogen/deuterium exchange mass spectrometry." Anal. Bioanal. Chem. (2014) 406 6541-6558. (Year: 2014).*
Kahsai, Alem W. et al. "Monitoring protein conformational changes and dynamics using stable-isotope labeling and mass spectrometry (CDSiL-MS)." Nat. Protoc. (2014) 9 1301-1319. (Year: 2014).*
Amezcua, C. and Szabo, C., Assessment of Higher Order Structure Comparability in Therapeutic Proteins Using Nuclear Magnetic Resonance Spectroscopy, Journal of Pharmaceutical Sciences, 102(6):1724-1733 (2013).
Bern, M. et al., Byonic: advanced peptide and protein identification software, Curr Protoc Bioinformatics, Chapter 13:Unit13.20 (2012).
Chick, J. et al., A mass-tolerant database search identifies a large proportion of unassigned spectra in shotgun proteomics as modified peptides, Nat Biotechnol., 33(7):743-9 (2015).
Creasy, D. and Cottrell, J., Error tolerant searching of uninterpreted tandem mass spectrometry data, Proteomics, 2(10):1426-34 (2002).
Demarest, S. and Glaser, S., Antibody therapeutics, antibody engineering, and the merits of protein stability, Curr Opin Drug Discov Devel., 11(5):675-87 (2008).
Fast, J. et al., Physical instability of a therapeutic Fc fusion protein: domain contributions to conformational and colloidal stability, Biochemistry, 48(49):11724-36 (2009).
Geiger, T. and Clarke, S., Deamidation, isomerization, and racemization at asparaginyl and aspartyl residues in peptides, Succinimide-linked reactions that contribute to protein degradation, J Biol Chem., 262(2):785-94 (1987).
Ghirlando, R. et al., Glycosylation of human IgG-Fc: influences on structure revealed by differential scanning micro-calorimetry, Immunol Lett., 68(1):47-52 (1999).
Houde, D. et al., Rapid characterization of IgG1 conformation and conformational dynamics by hydrogen/deuterium exchange mass spectrometry, Anal Chem., 81(7):2644-2651 (2009).
Hu, S. et al., Comparison of the Inhibition Mechanisms of Adalimumab and Infliximab in Treating Tumor Necrosis Factor a—Associated Diseases from a Molecular View, The Journal of Biological Chemistry, 288(38):27059-27067 (2013).
Huang, L. et al., In vivo deamidation characterization of monoclonal antibody by LC/MS/MS, Anal Chem., 77(5):1432-9 (2005).
International Search Report for PCT/US16/30994, 2 pages (dated Aug. 18, 2016).

(Continued)

*Primary Examiner* — Christopher Adam Hixson
(74) *Attorney, Agent, or Firm* — Choate, Hall & Stewart, LLP; Brenda Herschbach Jarrell; Rolando Medina

(57) ABSTRACT

Characterization and production of protein preparations, e.g., therapeutic glycoprotein preparations, are described.

21 Claims, 8 Drawing Sheets

(56) References Cited

OTHER PUBLICATIONS

International Search Report for PCT/US2016/031298, 2 pages (dated Aug. 12, 2016).
Kosky, A. et al., The effects of alpha-helix on the stability of Asn residues: deamidation rates in peptides of varying helicity, Protein Sci., 8(11):2519-23 (1999).
Liu, H. et al., Effect of posttranslational modifications on the thermal stability of a recombinant monoclonal antibody, Immunol Lett., 106(2):144-53 (2006).
Liu, H. et al., In vitro and in vivo modifications of recombinant and human IgG antibodies, Mabs, 6(5):1145-54 (2014).
Liu, Y. et al., Human antibody Fc deamidation in vivo, Biologicals, 37(5):313-22 (2009).
Luo, Q. et al., Chemical modifications in therapeutic protein aggregates generated under different stress conditions, J Biol Chem., 286(28):25134-44 (2011).
Pitt, James J., Principles and applications of liquid chromatography-mass spectrometry in clinical biochemistry, Clin Biochem Rev., 30(1):19-34 (2009).
Quinternet, M. et al., Heteronuclear NMR provides an accurate assessment of therapeutic insulin's quality, Journal of Pharmaceutical and Biomedical Analysis, 78-79:252-254 (2013).
Robinson, N. and Robinson, A., Deamidation of human proteins, Proc Natl Acad Sci USA, 98(22):12409-13 (2001).
Ross, P. et al., Multiplexed protein quantitation in *Saccharomyces cerevisiae* using amine-reactive isobaric tagging reagents, Mol Cell Proteomics, 3(12):1154-69 (2004).
Stamper, C. et al., Crystal structure of the B7-1/CTLA-4 complex that inhibits human immune responses, Nature, 410:608-611 (2001).
Takata, T. et al., Deamidation destabilizes and triggers aggregation of a lens protein, betaA3-crystallin, Protein Sci., 17(9):1565-75 (2008).
Tsubokawa, D. et al., A monoclonal antibody, PGM34, against 6-sulfated blood-group H type 2 antigen, on the carbohydrate moiety of mucin, the FEBS Journal, 274:1833-1848 (2007).
Venable, J. et al., Isotope-Coded Labeling for Accelerated Protein Interaction Profiling Using MS, Analytical Chemistry, 87:7540-7544 (2015).
Wright, H. and Urry, D., Nonenzymatic deamidation of asparaginyl and glutaminyl residues in proteins, Crit Rev Biochem Mol Biol., 26(1):1-52 (1991).
Written Opinion for PCT/US16/30994, 10 pages (dated Aug. 18, 2016).
Written Opinion for PCT/US2016/031298, 4 pages (dated Aug. 12, 2016).
Yang, Y. et al., Detecting low level sequence variants in recombinant monoclonal antibodies, Mabs, 2(3):285-98 (2010).
Zhang, X. et al., Crysal structure of the receptor-binding domain of human B7-2: Insights into organization and signaling, PNAS, 100(5):2586-2591 (2003).
Zhou, Y. and Vachet, R., Covalent Labeling with Isotopically Encoded Reagents for Faster Structural Analysis of Proteins by Mass Spectrometry, Analytical Chemistry, 85:9664-9670 (2013).
Madsen, J. et al., Covalent Labeling Denaturation Mass Spectrometry for Sensitive Localized Higher Order Structure Comparisons, Analytical Chemistry, 88:2478-2488 (2016).

\* cited by examiner

METHODS OF GLYCOPROTEIN ANALYSIS

CROSS REFERENCE TO RELATED APPLICATIONS

This application is the National Stage of International Application PCT/US2016/030994, filed May 5, 2016, which claims the benefit of U.S. Provisional Application No. 62/157,926, filed May 6, 2015, and of U.S. Provisional Application No. 62/220,081, filed Sep. 17, 2015, the contents of both all of which are hereby incorporated herein in their entireties.

BACKGROUND

Therapeutic polypeptides are an important class of therapeutic biotechnology products, and therapeutic antibodies (including murine, chimeric, humanized and human antibodies and fragments thereof) account for the majority of therapeutic biologic products.

SUMMARY OF THE INVENTION

The present disclosure provides, in part, methods for evaluating, identifying, analyzing and/or producing (e.g., manufacturing) a protein, e.g., a glycoprotein, e.g., an antibody and/or a biosimilar antibody. In some instances, methods herein allow highly resolved evaluation of a protein (e.g., a glycoprotein, e.g., an antibody) useful for, inter alia, manufacturing and/or evaluating a protein such as a biosimilar antibody.

In certain aspects, the disclosure provides methods of manufacturing. Such methods can include providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test protein (e.g., a test protein drug substance, e.g., a batch of a test protein drug substance); exposing a sample of the test protein (e.g., test protein drug substance) in a first state to a stressor to obtain a labeled test protein in a second state; acquiring (e.g., detecting, measuring, determining, receiving, or obtaining) or using mass spectrometry to acquire (e.g., detect, measure, determine, receive, or obtain) a test MS signal of the labeled test protein; comparing the test MS signal to a target MS signal for a target protein (e.g., target protein drug product) exposed to the same stressor, e.g., wherein the target protein is approved under a primary approval process; and processing the batch of the test protein (e.g., test protein drug substance) as drug product if the test MS signal and the target MS signal are tolerable; or taking an alternative action if the test MS signal and the target MS signal are not tolerable.

In some embodiments, using mass spectrometry comprises digesting the labeled test protein to produce a plurality of labeled test peptides.

In some embodiments, the stressor is a label. In some embodiments, the label is an isobaric label. In some embodiments, the method further includes labeling the test protein and/or the target protein with the label. In some embodiments, the method further comprises acquiring (e.g., detecting, measuring, determining, receiving, or obtaining) or using mass spectrometry to acquire (e.g., detect, measure, determine, receive, or obtain) the target MS signal.

In some embodiments, the test MS signal and the target MS signal are tolerable if they meet a predetermined value described herein. In some embodiments, the test MS signal and the target MS signal are tolerable if a peptide level obtained from the test MS signal and a corresponding peptide level obtained from the target MS signal differ by no more than about 10% (e.g., no more than about 9%, 8%, 7%, 6%, 5%, 4%, 3%, 2%, 1%, or less).

In some embodiments, the first state is a native state (e.g., a state of a protein in standard, conventional, and/or customary storage conditions for the protein, or in standard, conventional, and/or customary conditions for acquiring a signal, e.g., an MS signal). In some embodiments, the first state is a native state and the second state is a non-native state (e.g., a state of a protein in non-standard, non-conventional, and/or non-customary storage conditions for the protein, or in non-standard, non-conventional, and/or non-customary conditions for acquiring a signal, e.g., an MS signal).

In some embodiments, the target protein has an amino acid sequence that is 100% identical to the test protein, and wherein the target protein is approved under a BLA. In some embodiments, the target protein has an amino acid sequence with at least 85% identity (e.g., 90, 95, 98, 99, or 100%) identity to the test protein.

In some embodiments, the test MS signal comprises a plurality of signals from an MS spectrum of the test protein, and the target MS signal comprises a plurality of signals from an MS spectrum of the target protein. In some embodiments, an MS signal (e.g., a test MS signal and a target MS signal) comprises one or more peaks of an MS spectrum, e.g., about 1-100 peaks (or signals therein), e.g., about 5, 10, 15, 20, 25, 30, 35, 40, 45, 50, 55, 60, 65, 70, 75, 80, 85, 90, 95, 100, or more, peaks (or signals therein).

In some embodiments, the test protein (e.g., test protein drug substance) and the target protein (e.g., target protein drug product) are glycoproteins. In some embodiments, the test protein and the target protein are antibodies or antibody fragments, e.g., Fab fragments and/or Fc fragments. In some embodiments, the test protein and the target protein are Fc fusion proteins, or fragments thereof.

In some embodiments, the method comprises providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a second sample of the test protein (e.g., a test protein drug substance, e.g., a second batch of test protein drug substance); exposing the second sample of the test protein (e.g., test protein drug substance) in the first state to a second stressor to obtain a labeled test protein in a third state; acquiring (e.g., detecting, measuring, determining, receiving, or obtaining) or using mass spectrometry to acquire (e.g., detect, measure, determine, receive, or obtain) a second test MS signal of the labeled test protein; comparing the second test MS signal to a second target MS signal for the target protein (e.g., target protein drug product) exposed to the same stressor; and processing the second sample (e.g., second batch) of the test protein (e.g., test protein drug substance) as drug product if the second test MS signal and the second target MS signal are tolerable; or taking an alternative action if the second test MS signal and the second target MS signal are not tolerable.

In some embodiments, the second stressor comprises a second level of label. In some embodiments, the second level of label is a level (e.g., concentration) at least 2, 3, 4, 5, 6, 7, 8, 9, 10, 15, 20, 30, 40, 50, 60, 70, 80, 90, 100, or more, times greater than an initial level (e.g., concentration) of label used as an initial stressor. In some embodiments, the second level of label is a level (e.g., concentration) at least 2, 3, 4, 5, 6, 7, 8, 9, 10, 15, 20, 30, 40, 50, 60, 70, 80, 90, 100, or more, times less than an initial level (e.g., concentration) of label used as an initial stressor.

In some instances, the processing step includes combining the test protein with an excipient or buffer. In some embodiments, the processing step includes, but is not limited to, one or more of: formulating the test protein; processing the test protein into a drug product; combining the test protein with a second component, e.g., an excipient or buffer; changing the concentration of the test protein in a preparation; lyophilizing the test protein; combining a first and second aliquot of the test protein to provide a third, larger, aliquot; dividing the test protein into smaller aliquots; disposing the test protein into a container, e.g., a gas or liquid tight container; packaging the test protein; associating a container comprising the test protein with a label (e.g., labeling); shipping or moving the test protein to a different location.

In some embodiments, the alternative action comprises one or more of disposing of the test protein (e.g., test protein drug substance, e.g., batch of test protein drug substance), classifying for disposal the test protein (e.g., test protein drug substance, e.g., batch of test protein drug substance), labeling the test protein (e.g., test protein drug substance, e.g., batch of test protein drug substance) for disposal, and reprocessing the test protein (e.g., test protein drug substance, e.g., batch of test protein drug substance).

In another aspect, the disclosure provides methods of manufacture. Such methods can include providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test protein (e.g., a test protein drug substance, e.g., a batch of a test protein drug substance); labeling a sample of the test protein in a first state with a first label (e.g., a first isobaric label of a pair of isobaric labels) to obtain a labeled test protein in a second state; providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a target protein (e.g., a target protein drug product); labeling a sample of the target protein in a first state with a second label (e.g., a second isobaric label of a pair of isobaric labels) to obtain a labeled target protein in a second state; acquiring (e.g., detecting, measuring, determining, receiving, or obtaining) or using mass spectrometry to acquire (e.g., detect, measure, determine, receive, or obtain) a first level of a test peptide labeled with the first label and a second level of a corresponding target peptide labeled with the second label; comparing the first level and the second level; and processing the batch of the test protein drug substance as drug product if the first level and the second level are tolerable; or taking an alternative action if the first level and the second level are not tolerable.

In some embodiments, the method further includes determining a plurality of first levels for a plurality of test peptides labeled with the first label, and determining a plurality of second levels for a plurality of corresponding target peptides labeled with the second label. In some embodiments, the plurality of peptides comprises about 1-100, e.g., about 5, 10, 15, 20, 25, 30, 35, 40, 45, 50, 55, 60, 65, 70, 75, 80, 85, 90, 95, 100, or more, peptides.

In some embodiments, the method further includes labeling a second sample of the test protein in the first state with a second level of the first label to obtain a labeled test protein in a third state, and labeling a second sample of the target protein in the first state with a second level of the second label to obtain a labeled target protein in a third state.

In some embodiments, using mass spectrometry comprises digesting the labeled test protein and/or labeled target protein to produce a plurality of labeled test peptides and/or labeled target peptides.

In some embodiments, the first level and second level are tolerable if they meet a predetermined value described herein. In some embodiments, the first level and second level are tolerable if they differ by no more than about 10% (e.g., no more than about 9%, 8%, 7%, 6%, 5%, 4%, 3%, 2%, 1%, or less).

In some embodiments, the first state is a native state (e.g., a state of a protein in standard, conventional, and/or customary storage conditions for the protein, or in standard, conventional, and/or customary conditions for acquiring a signal, e.g., an MS signal). In some embodiments, the first state is a native state and the second state is a non-native state (e.g., a state of a protein in non-standard, non-conventional, and/or non-customary storage conditions for the protein, or in non-standard, non-conventional, and/or non-customary conditions for acquiring a signal, e.g., an MS signal).

In some embodiments, the target protein has an amino acid sequence that is 100% identical to the test protein, and wherein the target protein is approved under a BLA. In some embodiments, the target protein has an amino acid sequence with at least 85% identity (e.g., 90, 95, 98, 99, or 100%) identity to the test protein.

In some embodiments, the test protein (e.g., test protein drug substance) and the target protein (e.g., target protein drug product) are glycoproteins. In some embodiments, the test protein and the target protein are antibodies or antibody fragments, e.g., Fab fragments and/or Fc fragments. In some embodiments, the test protein and the target protein are Fc fusion proteins, or fragments thereof.

In some instances, the processing step includes combining the test protein with an excipient or buffer. In some embodiments, the processing step includes, but is not limited to, one or more of: formulating the test protein; processing the test protein into a drug product; combining the test protein with a second component, e.g., an excipient or buffer; changing the concentration of the test protein in a preparation; lyophilizing the test protein; combining a first and second aliquot of the test protein to provide a third, larger, aliquot; dividing the test protein into smaller aliquots; disposing the test protein into a container, e.g., a gas or liquid tight container; packaging the test protein; associating a container comprising the test protein with a label (e.g., labeling); shipping or moving the test protein to a different location.

In some embodiments, the alternative action comprises one or more of disposing of the test protein (e.g., test protein drug substance, e.g., batch of test protein drug substance), classifying for disposal the test protein (e.g., test protein drug substance, e.g., batch of test protein drug substance), labeling the test protein (e.g., test protein drug substance, e.g., batch of test protein drug substance) for disposal, and reprocessing the test protein (e.g., test protein drug substance, e.g., batch of test protein drug substance).

In another aspect, the disclosure provides methods of manufacture. Such methods can include providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a test protein (e.g., a test protein drug substance, e.g., a batch of a test protein drug substance); labeling a sample of the test protein in a first state with a plurality of levels of (e.g., a plurality of difference concentrations of) a first label (e.g., a first isobaric label of a pair of isobaric labels) to obtain a plurality of labeled test protein in a second state; providing (e.g., producing or expressing (e.g., in small scale or large scale cell culture) or manufacturing) or obtaining (e.g., receiving and/or purchasing from a third party (including a contractually related third party or a non-contractually-related (e.g., an independent) third party) a target protein (e.g., a target protein drug product); labeling a sample of the target protein in a first state with a plurality of corresponding levels of (e.g., corresponding concentrations of, e.g., the same concentrations as those of the first label) of a second label (e.g., a second isobaric label of a pair of isobaric labels) to obtain a plurality of labeled target protein in a second state; for each level of label: acquiring (e.g., detecting, measuring, determining, receiving, or obtaining) or using mass spectrometry to acquire (e.g., detect, measure, determine, receive, or obtain) a first level of a test peptide labeled with the first label and a second level of a corresponding target peptide labeled with the second label; comparing the first level and the second level; and processing the batch of the test protein drug substance as drug product if for at least one level of label the first level and the second level are tolerable; or taking an alternative action if for at least one level of label the first level and the second level are not tolerable.

In some embodiments, the batch of the test protein drug substance is processed as drug product if for each level of label the first level and the second level are tolerable. In some embodiments, the alternative action is taken if for each level of label the first level and the second level are not tolerable.

In another aspect, the disclosure provides methods of manufacturing. Such methods can include labeling a first sample of a test protein with a first level of a label to obtain a first sample of labeled test protein in a first state; labeling a second sample of the test protein with a second level of the label to obtain a second sample of labeled test protein in a second state; obtaining labeled test peptides from the first sample and obtaining labeled test peptides from the second sample; using mass spectrometry to determine a first level of a labeled test peptide from the first sample and a second level of a corresponding labeled test peptide from the second sample; comparing the determined first and second levels of test peptides to corresponding first and second levels of target peptides of a target protein to determine whether the first and second levels of test peptides are tolerable; and processing the test protein as drug product if the first and second levels of test peptides are tolerable; or taking an alternative action if the first and second levels of test peptides are not tolerable.

In any of the aspects described herein, methods can further include, e.g., one or more of: memorializing a comparison and/or results of a comparison (e.g., between a test MS signal and a target MS signal) using a recordable medium (e.g., on paper or in a computer readable medium, e.g., in a Certificate of Testing, Material Safety Data Sheet (MSDS), batch record, or Certificate of Analysis (CofA)); informing a party or entity (e.g., a contractual or manufacturing partner, a care giver or other end-user, a regulatory entity, e.g., the FDA or other U.S., European, Japanese, Chinese or other governmental agency, or another entity, e.g., a compendial entity (e.g., U.S. Pharmacopoeia (USP)) or insurance company) of the comparison and/or results of the comparison.

Definitions

As used herein, a "glycoprotein" refers to amino acid sequences that include one or more oligosaccharide chains (e.g., glycans) covalently attached thereto. Exemplary amino acid sequences include peptides, polypeptides and proteins. Exemplary glycoproteins include glycosylated antibodies and antibody-like molecules (e.g., Fc fusion proteins). Exemplary antibodies include monoclonal antibodies and/or fragments thereof, polyclonal antibodies and/or fragments thereof, and Fc domain containing fusion proteins (e.g., fusion proteins containing the Fc region of IgG1, or a glycosylated portion thereof).

As used herein, a "glycoprotein preparation" is a composition or mixture that includes at least one glycoprotein. In some instances, a glycoprotein preparation (e.g., such as a glycoprotein drug substance or a precursor thereof) can be a sample from a proposed or test batch of a drug substance or drug product.

As used herein, a "batch" of a glycoprotein preparation refers to a single manufacturing run of the glycoprotein. Evaluation of different batches thus means evaluation of different manufacturing runs or batches.

As used herein, "sample(s)" refer to separately procured samples. In some embodiments, evaluation of separate samples includes evaluation of different commercially available containers or vials of the same batch or from different batches.

As used herein, "acquire" or "acquiring" (e.g., "acquiring information") means obtaining possession of a physical entity, or a value, e.g., a numerical value, by "directly acquiring" or "indirectly acquiring" the physical entity or value. "Directly acquiring" means performing a process (e.g., performing an assay or test on a sample) to obtain the physical entity or value. "Indirectly acquiring" refers to receiving the physical entity or value from another party or source (e.g., a third party laboratory that directly acquired the physical entity or value). "Directly acquiring" a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Directly acquiring" a value includes performing a process that includes a physical change in a sample or another substance, e.g., performing an analytical process (e.g., an MS process) which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, the term "approximately" or "about," as applied to one or more values of interest, refers to a value that is similar to a stated reference value. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

In general, a "protein", as used herein, is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

The term "protein preparation" as used herein refers to a mixture of proteins obtained according to a particular production method. The proteins in a protein preparation may be the same or different, i.e., a protein preparation may include several copies of the same protein and/or a mixture of different proteins. The production method will generally include a recombinant preparation step using cultured cells that have been engineered to express the proteins in the protein preparation (or to express the proteins at a relevant level or under relevant conditions). The production method may further include an isolation step in which proteins are isolated from certain components of the engineered cells (e.g., by lysing the cells and pelleting the protein component by centrifugation). The production method may also include a purification step in which the proteins in the protein preparation are separated (e.g., by chromatography) from other cellular components, e.g., other proteins or organic components that were used in earlier steps. It will be appreciated that these steps are non-limiting and that any number of additional productions steps may be included. Different protein preparations may be prepared by the same production method but on different occasions (e.g., different batches). Alternatively, different protein preparations may be prepared by different production methods. Two production methods may differ in any way (e.g., expression vector, engineered cell type, culture conditions, isolation procedure, purification conditions, etc.).

As used herein, the terms "biologic", "biotherapeutic", and "biologic product" are used interchangeably to refer to peptide and protein products. For example, biologics herein include naturally derived or recombinant products expressed in cells, such as, e.g., proteins, glycoproteins, fusion proteins, growth factors, vaccines, blood factors, thrombolytic agents, hormones, interferons, interleukin based products, monospecific (e.g., monoclonal) antibodies, therapeutic enzymes. Some biologics are approved under a "Biologics License Application" or "BLA", under section 351(a) of the Public Health Service (PHS) Act, whereas biosimilar and interchangeable biologics referencing a BLA as a reference product are licensed under section 351(k) of the PHS Act. Section 351 of the PHS Act is codified as 42 U.S.C. 262. Other biologics may be approved under section 505(b)(1) of the Federal Food and Cosmetic Act, or as abbreviated applications under sections 505(b)(2) and 505(j) of the Hatch Waxman Act, wherein section 505 is codified 21 U.S.C. 355.

As used herein, "approval" refers to a procedure by which a regulatory entity, e.g., the FDA or EMEA, approves a candidate for therapeutic or diagnostic use in humans or animals. As used herein, a "primary approval process" is an approval process which does not refer to a previously approved protein, e.g., it does not require that the protein being approved have structural or functional similarity to a previously approved protein, e.g., a previously approved protein having the same primary amino acid sequence or a primary amino acid sequence that differs by no more than 1, 2, 3, 4, 5, or 10 residues or that has 98% or more sequence identity. In embodiments the primary approval process is one in which the applicant does not rely, for approval, on data, e.g., clinical data, from a previously approved product. Exemplary primary approval processes include, in the U.S., a Biologics License Application (BLA), or supplemental Biologics License Application (sBLA), a New Drug Application (NDA) under 505(b)(1) of the Federal Food and Cosmetic Act, and in Europe an approval in accordance with the provisions of Article 8(3) of the European Directive 2001/83/EC, or an analogous proceeding in other countries or jurisdictions.

As used herein, a "secondary approval process" is an approval process that refers to clinical data for a previously approved product. In embodiments, a secondary approval requires that the product being approved have structural or functional similarity to a previously approved product, e.g., a previously approved protein having the same primary amino acid sequence or a primary amino acid sequence that differs by no more than 1, 2, 3, 4, 5, or 10 amino acid residues or that has at least 98%, 99% or more (100%) sequence identity. In embodiments a secondary approval process is one in which the applicant relies, for approval, on clinical data from a previously approved product. Exemplary secondary approval processes include, in the U.S., an approval under 351(k) of the Public Health Service Act or under section 505(j) or 505(b)(2) of the Hatch Waxman Act and in Europe, an application in accordance with the provisions of Article 10, e.g., Article 10(4), of the European Directive 2001/83/EC, or an analogous proceeding in other countries or jurisdictions.

As used herein, a "target protein" is any protein of interest to which comparison with a second or "test" protein is desired. An exemplary target protein is an antibody, e.g., a CDR-grafted, humanized or human antibody. Other target proteins include glycoproteins, cytokines, hematopoietic proteins, soluble receptor fragments, growth factors, and glycoprotein conjugates (e.g., Fc fusion proteins). In some embodiments, a target protein is a commercially available, or approved, biologic that defines or provides the basis against which a test protein is measured or evaluated. In embodiments a target protein is commercially available for therapeutic use in humans or animals. In embodiments a target protein was approved for use in humans or animals by a primary approval process. In embodiments a target protein is a reference listed drug for a secondary approval process. Exemplary target proteins include those described herein.

An "MS signal", as used herein, refers to one or more signals or representations obtained from MS and associated with presence of one or more chemical compounds and/or structural characteristics and/or peptides. In some embodiments, an MS signal is a peak, or point therein, in an MS spectrum. In some embodiments, an MS signal is a plurality of peaks, or points therein, in an MS spectrum.

As used herein, a "stressor" refers to any agent or condition that induces a shift of a protein from a first state to a second state. In some instances, a stressor can induce a conformational change of a protein, e.g., can induce a change from a first conformation to a second conformation. In some embodiments, a stressor is a label (e.g., an isobaric label). Exemplary isobaric labels include, without limitation, TMTs, iTRAQs, and ICATs.

"Tolerable", as used herein, refers to a range of acceptability for one or more pairs of compared MS signals, e.g., an MS signal of test protein and a corresponding MS signal of a target protein. In some instances, a comparison herein is an assessment or measure of variability between an MS signal of a test protein and an MS signal of a target protein, and such compared MS signals are tolerable if the variability between them does not exceed (e.g., as determined using a given statistical method) the variability of MS signals determined for multiple distinct batches (e.g., 2, 3, 4, 5, or more batches) of such target protein, e.g., assessed using the same MS and stressor (e.g., label or level of label). In some instances, a comparison is tolerable if it meets a predetermined value (e.g., obtained by assessing multiple batches of target protein, as described above). In some instances, comparison of MS signals is performed using a representation. In some instances, a representation is a ratio of a level of a peptide obtained from an MS signal from a test protein and a level of a corresponding peptide obtained from an MS signal from a target protein, and compared MS signals are tolerable if such a ratio is about 2, 1.9, 1.8, 1.7, 1.6, 1.5, 1.4, 1.3, 1.2, 1.1, or 1. In some instances, a representation is a ratio of a level of a peptide obtained from an MS signal from a target protein and a level of a corresponding peptide obtained from an MS signal from a test protein, and compared MS signals are tolerable if such a ratio is about 2, 1.9, 1.8, 1.7, 1.6, 1.5, 1.4, 1.3, 1.2, 1.1, or 1.

The term "corresponding peptides", as used herein, refers to two or more peptides having the same amino acid sequence. In some embodiments, corresponding peptides refer to peptides from different samples of the same protein (e.g., a test protein or a target protein) having the same amino acid sequence. In some embodiments, corresponding peptides refer to peptides from a test protein and a target protein having the same amino acid sequence. For example, a peptide from a test protein and a peptide from a target protein are corresponding peptides if they have the same amino acid sequence.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way. The present application also incorporates by reference the entire contents of a U.S. Provisional Application No. 62/157,922, filed on May 6, 2015.

These, and other aspects of the invention, are described in more detail below and in the claims.

DETAILED DESCRIPTION

Figure 1A:
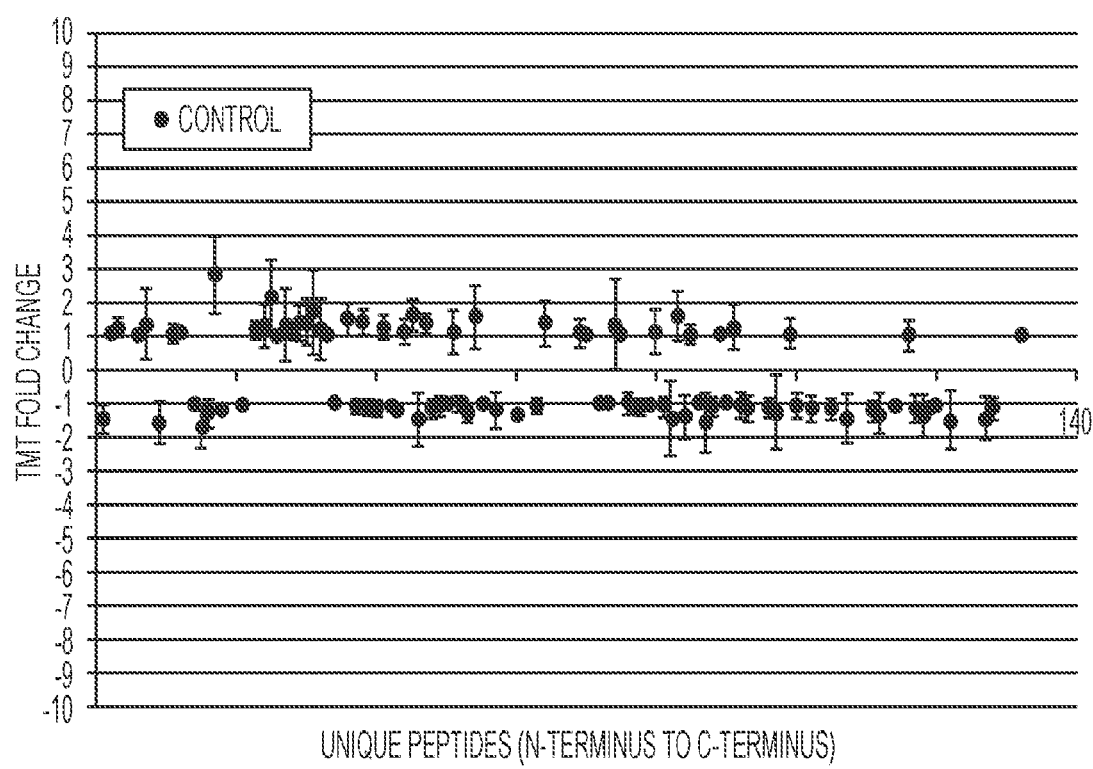
FIG. 1A is a representation of differences of relative levels of labeled peptides from a model Fc fusion protein.

The present disclosure is based, in part, on the discovery that assessment by MS of the behavior of a labeled protein can be used to predict biosimilarity, e.g., to manufacture biosimilar proteins (wherein a biosimilar protein is a protein approved for use in humans by a secondary approval process). For example, the present disclosure describes that MS can be used to assess the behavior of a target protein after being labeled and that such behavior can be compared to the behavior of a test protein after being labeled with the same label or same level of label, and that biosimilarlity can be determined if the two compared behaviors are tolerably comparable.

In some methods of the disclosure, labeling of a protein with an isobaric label (e.g., different levels of isobaric label) can induce one or more conformational changes to the higher-order structure of a protein (e.g., shifts from a first state to a second state), which can be assessed using MS methods. In some instances, such shifts of a test protein can be compared to corresponding shifts of a target protein in order to assess biosimilarity. Accordingly, the present disclosure provides strategies to assess biosimilarity of a protein (e.g., an antibody) to a target protein (e.g., a target antibody), e.g., during one or more stages of process development and/or production of a biosimilar product.

Analysis Methods

Labeling of a protein as described herein can induce a shift in the protein from a first state to a second state, which can be assessed using MS methods. In some instances, such a shift of a test protein from a first state to a second state can be compared to a corresponding shift of a target protein from a first state to a second state, e.g., to assess a level of similarity between the test and target proteins. Thus, in some embodiments, a level of a peptide from a labeled test protein (e.g., labeled with a first label) is determined by MS and is compared with a level of a corresponding peptide from a labeled target protein (e.g., labeled with a second label), and a difference in the peptide levels is determined, e.g., to assess a level of similarity between the test protein and the target protein. In some instances, a plurality of peptides labeled with the first label are compared to a plurality of corresponding peptides labeled with the second label.

Methods described herein utilize mass spectrometry (MS). Mass spectrometry obtains molecular weight and structural information on chemical compounds by ionizing the molecules and measuring either their time-of-flight or the response of the molecular trajectories to electric and/or magnetic fields. The methods of the present disclosure employ conventional mass spectrometry techniques known to those of skill in the art, and any known MS method can be adapted for use in methods of the disclosure. Exemplary MS include, but are not limited to, tandem MS (MS/MS), LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Such methods are described in, e.g., Pitt, Clin. Biochem. Rev. 30:19-34 (2009). Mass spectrometers are known in the art and are commercially available from, e.g., Agilent Inc., Bruker Corporation, and Thermo Scientific.

Methods described herein involve use of labels for MS analysis, and any label known in the art to be useful in MS can be used. In some instances, labels are added (e.g., coupled using an amine-reactive or a thiol-reactive chemistry) to a protein (e.g., via amine or thiol groups of proteins) using known methods. In certain embodiments, a label is a compound that includes a peptide reactive group (e.g., a maleimide moiety, a bromoacetamide moiety, a pyridyldithio moiety, an iodoacetamide moiety, a methanethiosulfonate moiety, an isothiocyanate moiety, and/or an N-hydroxysuccinimide ester moiety).

In some instances, isobaric labels are used. For example, isobaric labels can be used to label amines in proteins and peptides prior to mixing and simultaneous analysis of multiple samples. Isobaric labels are known in the art and generally have the same chemical structure but different isotopic combinations in the mass reporter. Isobaric labels include, for example, Tandem Mass Tags (TMT) and Isobaric tags for relative and absolute quantitation (iTRAQ) (Ross et al., Molecular & Cellular Proteomics, 2004, 3, 1154-1169). TMT and iTRAQ reagents use a pair of mass tags bearing a differential incorporation of carbon and nitrogen isotopes. Two samples are labelled with either the heavy or light tag and then mixed prior to analysis by MS (e.g., LC-MS). A peptide present in both samples will give a pair of precursor ions with the same mass, but with different mass tags after MS/MS. TMT and iTRAQ isobaric labels are commercially available from, e.g., Life Technologies (Carlsbad, Calif.) and Sciex (Framingham, Mass.), respectively.

Other isobaric labels such as isotope-coded affinity tags (ICAT) as well as nonisobaric labels known in the art can be used to compare the higher structure of two protein samples as long as a protein conformation change is induced upon labeling. In some instances, a protein (e.g., a test protein and/or a target protein) is subjected to cleavage, e.g., by limited proteolysis and/or chemical cleavage. For example, a protein can be subjected to enzymatic digestion using known enzymes including, but not limited to, trypsin, papain, pepsin, or Lys-C protease. In some instances, chemical cleavage is performed by reducing disulfide bonds in the protein. For example, reduction of disulfide bonds can include contacting a sample with a reducing agent (e.g., dithiothreitol, mercaptoethanol, tributylphosphine, and/or tri(2-carboxyethyl)phosphine hydrochloride).

In some instances, higher-order structure of a protein is assessed by performing MS on a protein (e.g., a sample of a protein preparation) to obtain a mass spectrum of relative abundance of ions with a particular mass/charge over a given range (e.g., 100 to 2000 amu). Numerous methods for relating amount of an ion to an amount of a peptide are known to those of ordinary skill in the art. For example, relative abundance of a given ion may be compared to a table that converts that relative abundance to an absolute amount of a peptide. Alternatively, external standards may be run with samples, and a standard curve constructed based on ions generated from such standards. Using a standard curve, relative abundance of a given ion may be converted into an absolute amount of a peptide. Methods of generating and using such standard curves are well known in the art, and one of ordinary skill is capable of selecting an appropriate internal standard.

In some instances, multiple samples of a protein (e.g., multiple samples of a test protein and/or a target protein) can be labeled with a plurality of isobaric labels having different mass tags (e.g., 2, 3, 4, 5, 6, 7, 8, 9, 10, 11, 12, 13, 14 or more labels having different mass tags). In some instances, the plurality of isobaric labels is an "x-plex" of TMT labels, such as a duplex, a "sixplex", a "10-plex" or a "12-plex". In one exemplary method, a sixplex of TMT labels is used, each label having a different mass (e.g., 126, 127, 128, 129, 130, and 131). For example, each of three samples of a test protein in a first state can be independently labeled with one of three TMT labels (e.g., 126, 127, and 128), and each of three samples of a test protein in a second state can be independently labeled with three different TMT labels (e.g., 129, 130, and 131). Use of such TMT sixplex procedure allows three replicates of a test protein in a first state and three replicates of a test protein in a second state to be analyzed using a single MS sample preparation and one MS run. Without wishing to be bound by theory, it is believed that because of such multiplexing capability, variability from differences in, e.g., MS ionization, data-dependent peak picking, and/or sample preparation is reduced, improving repeatability and/or robustness.

In some instances, levels of corresponding labeled peptides (e.g., labeled peptides from a test protein and corresponding labeled peptides from a target protein) are obtained, identified, assessed, measured, determined and/or quantified. Such levels can be compared to determine a level of similarity between a test protein and a target protein. In some instances, two MS signals (e.g., a test protein MS signal and a target protein MS signal) are tolerable if a level of one or more peptides from a test protein and a level of one or more corresponding peptides from a target protein differ by no more than about 20%, 19%, 18%, 17%, 16%, 15%, 14%, 13%, 12%, 11%, 10%, 9%, 8%, 7%, 6%, 5%, 4%, 3%, 2%, or 1%, or less. In some instances, two MS signals (e.g., a test protein MS signal and a target protein MS signal) are tolerable if one or more ratios of a level of a peptide from a test protein to a level of a corresponding peptide from a target protein, or one or more ratios of a level of a peptide from a target protein to a level of a corresponding peptide from a test protein, is between about 3 and about 1 (e.g., between about 2 and about 1, e.g., between about 1.5 and about 1), e.g., is about 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1.

In one exemplary method, MS is used to assess the similarity of a test biologic to a reference biologic that is approved under a BLA. In an exemplary method, a reference biologic and a test biologic are labeled separately with amine-reactive isobaric labels, which upon dissociation (e.g., by MS/MS) yield reporter ions of different mass. In a next step, labeled proteins are sequentially mixed about 1:1, denatured, reduced, alkylated, enzymatically digested, and analyzed by LC-MS/MS. Peptides are identified by database searching MS/MS spectra, and reporter ion ratios are used to calculate fold changes (i.e., localized structural deviations) for each labeled peptide. While some methods described herein recite a particular order of steps (e.g., labeling, denaturing, reducing, alkylating, and/or digesting), in some instances, one or more steps can be performed in a different order. For example, in some methods, proteins are digested before being labeled.

In some instances, proteins are labeled to induce a shift in the protein from a first state to a second state, and are also exposed to one or more additional stressor(s) described herein to induce further conformational changes of a protein.

Applications

In some instances, methods disclosed herein can be used to confirm the identity and/or quality of a protein, e.g., glycoprotein preparation. For example, methods can include assessing preparations (e.g., samples, lots, and/or batches) of a test protein, e.g., to confirm whether the test protein qualifies as a target protein, and, optionally, qualifying the test protein as a target protein if qualifying criteria (e.g. predefined qualifying criteria) are met; thereby evaluating, identifying, and/or producing (e.g., manufacturing) a protein product.

Methods of the disclosure have a variety of applications and include, e.g., quality control at different stages of manufacture, analysis of a protein preparation prior to and/or after completion of manufacture (e.g., prior to or after distribution to a fill/finish environment or facility), prior to or after release into commerce (e.g., before distribution to a pharmacy, a caregiver, a patient, or other end-user). In some instances, a protein preparation is a drug substance (an active pharmaceutical ingredient or "API") or a drug product (an API formulated for use in a subject such as a human patient). In some instances, a protein preparation is from a stage of manufacture or use that is prior to release to care givers or other end-users; prior to packaging into individual dosage forms, such as syringes, pens, vials, or multi-dose vials; prior to determination that the batch can be commercially released, prior to production of a Certificate of Testing, Material Safety Data Sheet (MSDS) or Certificate of Analysis (CofA) of the preparation. In some instances, a protein preparation is from an intermediate step in production, e.g., it is after secretion of a protein from a cell but prior to purification of drug substance.

Evaluations from methods described herein are useful for guiding, controlling or implementing a number of activities or steps in the process of making, distributing, and monitoring and providing for the safe and efficacious use of a protein preparation. Thus, in an embodiment, e.g., responsive to the evaluation, e.g., depending on whether a criterion is met, a decision or step is taken. The method can further comprise one or both of the decision to take the step and/or carrying out the step itself. E.g., the step can comprise one in which the preparation (or another preparation for which the preparation is representative) is: classified; selected; accepted or discarded; released or processed into a drug product; rendered unusable for commercial release, e.g., by labeling it, sequestering it, or destroying it; passed on to a subsequent step in manufacture; reprocessed (e.g., the preparation may undergo a repetition of a previous process step or subjected to a corrective process); formulated, e.g., into drug substance or drug product; combined with another component, e.g., an excipient, buffer or diluent; disposed into a container; divided into smaller aliquots, e.g., unit doses, or multi-dose containers; combined with another preparation of the protein; packaged; shipped; moved to a different location; combined with another element to form a kit; combined, e.g., placed into a package with a delivery device, diluent, or package insert; released into commerce; sold or offered for sale; delivered to a care giver or other end-user; or administered to a subject. E.g., based on the result of the determination or whether one or more subject entities is present, or upon comparison to a reference standard, the batch from which the preparation is taken can be processed, e.g., as just described.

Methods described herein may include making a decision: (a) as to whether a protein preparation may be formulated into drug substance or drug product; (b) as to whether a protein preparation may be reprocessed (e.g., the preparation may undergo a repetition of a previous process step); and/or (c) that the protein preparation is not suitable for formulation into drug substance or drug product. In some instances, methods comprise: formulating as referred to in step (a), reprocessing as referred to in step (b), or rendering the preparation unusable for commercial release, e.g., by labeling it or destroying it, as referred to in step (c).

Test Proteins and Target Proteins

Methods described herein can be used to make and/or evaluate a test protein preparation, e.g., a test biologic preparation. In some embodiments, a test protein is a test biologic being evaluated for similarity to a target protein, e.g., a target biologic. A test biologic may or may not be commercially available. In some embodiments, a test biologic is not commercially available for therapeutic use in humans or animals. In some embodiments, a test biologic has not been approved for therapeutic or diagnostic use in humans or animals. In some embodiments, a test biologic has been approved, e.g., under a secondary approval process, for therapeutic or diagnostic use in humans or animals. In some embodiments, a test protein (e.g., test biologic) has the same primary amino acid sequence as a target protein (e.g., target biologic) or will differ by no more than 1, 2, 3, 4, 5, 10, 15, 20, 25, 30 residues and/or has at least 90, 95, 98, 99% or is identical to a target protein sequence (e.g., target biologic sequence). The terms the "same primary amino acid sequence", "a primary amino acid sequence that differs by no more than 1, 2, 3, 4, 5, 10, 15, 20, 25, or 30 residues", "sequences that have at least 98% or more sequence identity", or similar terms, relate to level of identity between a primary amino acid sequence, e.g., of first protein, e.g., a test protein, and a primary amino acid sequence, e.g., of second protein, e.g., a target protein. In some embodiments, a protein preparation or product includes amino acid variants, e.g., species that differ at terminal residues, e.g., at one or two terminal residues. In some embodiments of such cases, sequence identity compared is the identity between the primary amino acid sequence of the most abundant (e.g., most abundant active) species in each of the products being compared. In some embodiments, sequence identity refers to the amino acid sequence encoded by a nucleic acid that can be used to make the product.

Nonlimiting, exemplary target proteins can include abatacept (Orencia®, Bristol-Myers Squibb), abciximab (ReoPro®, Roche), adalimumab (Humira®, Bristol-Myers Squibb), aflibercept (Eylea®, Regeneron Pharmaceuticals), alefacept (Amevive®, Astellas Pharma), alemtuzumab (Campath®, Genzyme/Bayer), basiliximab (Simulect®, Novartis), belatacept (Nulojix®, Bristol-Myers Squibb), belimumab (Benlysta®, GlaxoSmithKline), bevacizumab (Avastin®, Roche), canakinumab (Ilaris®, Novartis), brentuximab vedotin (Adcetris®, Seattle Genetics), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), denosumab (Prolia®, Amgen; Xgeva®, Amgen), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), golimumab (Simponi®, Janssen), ibritumomab (Zevalin®, Spectrum Pharmaceuticals), infliximab (Remicade®, Centocor), ipilimumab (Yervoy™, Bristol-Myers Squibb), muromonab (Orthoclone OKT3®, Janssen-Cilag), natalizumab (Tysabri®, Biogen Idec, Elan), ofatumumab (Arzerra®, GlaxoSmithKline), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabThera®, Roche), tocilizumab (Actemra®, Genentech; RoActemra, Hoffman-La Roche) tositumomab (Bexxar®, GlaxoSmithKline), trastuzumab (Herceptin®, Roche), and ustekinumab (Stelara®, Janssen).

Antibodies

In some instances, test proteins and target proteins described herein are antibodies. As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda. In some embodiments, an antibody includes an Fc region. In some embodiments, an antibody is a therapeutic antibody.

Antibodies described herein can include, for example, monoclonal antibodies, polyclonal antibodies (e.g., IVIG), multi specific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

Antibodies or fragments thereof can be produced by any method known in the art for synthesizing antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using methods described in, e.g., Morrison, 1985, Science 229: 1202, and humanized antibodies by methods described in, e.g., U.S. Pat. No. 6,180,370.

Glycoprotein Conjugates

In some instances, test proteins and target proteins are glycoprotein conjugates (e.g., Fc regions or Fc fragments containing one or more N-glycosylation sites thereof that are conjugated or fused to one or more heterologous moieties). Heterologous moieties include, but are not limited to, peptides, polypeptides, proteins, fusion proteins, nucleic acid molecules, small molecules, mimetic agents, synthetic drugs, inorganic molecules, and organic molecules. In some instances, a glycoprotein conjugate is a fusion protein that comprises a peptide, polypeptide, protein scaffold, scFv, dsFv, diabody, Tandab, or an antibody mimetic fused to an Fc region, such as a glycosylated Fc region. A fusion protein can include a linker region connecting an Fc region to a heterologous moiety (see, e.g., Hallewell et al. (1989), J. Biol. Chem. 264, 5260-5268; Alfthan et al. (1995), Protein Eng. 8, 725-731; Robinson & Sauer (1996)).

Recombinant Gene Expression

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

In some embodiments, a protein described herein is produced using recombinant methods. Recombinant expression of a gene, such as a gene encoding a polypeptide, such as an antibody described herein, can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and transfected cells can then be cultured by conventional techniques to produce polypeptide.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the E. coli expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like, pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by inclusion of appropriate transcription enhancer elements, transcription terminators, etc. (see, e.g., Bittner et al., 1987, Methods in Enzymol. 153:516-544).

In addition, a host cell strain can be chosen that modulates expression of inserted sequences, or modifies and processes the gene product in the specific fashion desired. Different host cells have characteristic and specific mechanisms for post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NS0 (a murine myeloma cell line that does not endogenously produce any immunoglobulin chains), CRL7O3O and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

Once a protein described herein been produced by recombinant expression, it may be purified by any method known in the art for purification, for example, by chromatography (e.g., ion exchange, affinity, and sizing column chromatography), centrifugation, differential solubility, or by any other standard technique for purification of proteins. For example, an antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a glycoprotein can be fused to heterologous polypeptide sequences to facilitate purification. Glycoproteins having desired sugar chains can be separated with a lectin column by methods known in the art (see, e.g., WO 02/30954).

Pharmaceutical Compositions

A protein (e.g., an antibody) described herein can be incorporated into a pharmaceutical composition. Such a pharmaceutical composition is useful in the prevention and/or treatment of diseases. Pharmaceutical compositions comprising a polypeptide (e.g., an antibody) can be formulated by methods known to those skilled in the art (see, e.g., Remington's Pharmaceutical Sciences, 20th Ed., Lippincott Williams & Wilkins, 2000). The pharmaceutical composition can be administered parenterally in the form of an injectable formulation comprising a sterile solution or suspension in water or another pharmaceutically acceptable liquid. For example, the pharmaceutical composition can be formulated by suitably combining the polypeptide with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a polypeptide (e.g., antibody) can be selected from a range of 0.001 mg/kg of body weight to 1000 mg/kg of body weight. On the other hand, a dose can be selected in the range of 0.001 mg/kg of body weight to 100000 mg/kg of body weight, but the present disclosure is not limited to such ranges. The dose and method of administration varies depending on the weight, age, condition, and the like of the patient, and can be suitably selected as needed by those skilled in the art.

The disclosure is further illustrated by the following examples. The examples are provided for illustrative purposes only. They are not to be construed as limiting the scope or content of the disclosure in any way.

EXAMPLES

Example 1: Characterization of a Model Fc Fusion Protein

An isobaric tagging method was used to stress a model Fc fusion protein and to detect higher-order structure ("HOS") changes. For isobaric tagging, commercially available Tandem Mass Tags ("TMT") with reporter ions at m/z 126 and 127 were used (Life Technologies, Carlsbad, Calif.).

A label-stressed control mixture was first created. Fc fusion protein samples were diluted in an amine-free 1×PBS buffer at pH 7.4 with no denaturant. Two aliquots of the Fc fusion protein were allowed to equilibrate to room temperature. One aliquot was labelled with 100 µg "127" TMT reagent for 2 minutes, and one aliquot was labelled with 100 µg "126" TMT reagent for 2 minutes. The 126-labelled aliquot was mixed at 1:1 ratio with the 127-labelled aliquot after each reaction was completed to obtain a label-stressed control mixture.

Heat-stressed samples were produced by first diluting Fc fusion protein samples in an amine-free 1×PBS buffer at pH 7.4 with no denaturant. Fc fusion protein samples were analyzed under two heat-stressed conditions. A first sample was exposed to 55° C. for 18 hours, and a second sample was exposed to 75° C. for 18 hours. The samples were then labelled with the "127" TMT reagent at specified reaction times.

Separately, samples of Fc fusion protein were allowed to equilibrate to room temperature and were subsequently labelled with the "126" TMT reagent at the same specified reaction times used for the 55° C. and 75° C. samples. The 55° C. and 75° C. 127-labelled samples were mixed 1:1 with the label-stressed (i.e., 126-labelled) samples after each reaction was completed to produce a "55° C. mixture" and a "75° C. sample", respectively.

The label-stressed control mixture, the 55° C. mixture, and the 75° C. mixture were then denatured, reduced, alkylated, and enzymatically digested with chymotrypsin. The resulting peptides from each mixture were then analyzed by LCMS/MS. The following LC parameters were used:

| | |
|---|---|
| MOBILE PHASE A | 0.1% FORMIC ACID IN WATER |
| MOBILE PHASE B | 0.1% FORMIC ACID IN ACETONITRILE |
| COLUMN TEMP | 50° C. |
| FLOW RATE | 50 µL/MIN |
| INJECTION AMOUNT | 6 µL |
| COLUMN | ACQUITY UPLC BEH C18 COLUMN, 130 Å, 1.7 µM, 2.1 × 50 mm |

| TIME (MIN) | FLOW RATE (µL/MIN) | % A | % B | CURVE | SWITCHING VALVE CONFIGURATION |
|---|---|---|---|---|---|
| 0.0 | 50 | 96 | 4 | 5 | TO WASTE |
| 10.0 | 50 | 96 | 4 | 5 | TO MS |
| 20.0 | 50 | 92 | 8 | 5 | TO MS |
| 95.0 | 50 | 65 | 35 | 5 | TO MS |
| 100.0 | 50 | 5 | 95 | 5 | TO MS |
| 110.0 | 50 | 5 | 95 | 5 | TO MS |
| 112.0 | 50 | 96 | 4 | 5 | TO MS |
| 130.0 | 50 | 96 | 4 | 5 | TO MS |

The following MS conditions were used:

| SETTING | Q EXACTIVE ORBITRAP |
|---|---|
| SPRAY VOLTAGE (kV) | 3.32 |
| CAPILLARY TEMPERATURE (° C.) | 275 |
| SHEATH GAS FLOW | 15 |
| S-LENS RF LEVEL | 85 |

| SETTING | Q EXACTIVE ORBITRAP XCALIBUR SETTINGS |
|---|---|
| FULL MS | |
| MODE | DATA-DEPENDENT |
| SCAN RANGE (m/z) | 400-2000 |
| RESOLUTION | 35,000 |
| AGC TARGET | 1E6 |
| MICROSCANS | 1 |
| MAXIMUM INJECTION TIME (ms) | 250 ms |
| MS/MS | |
| DATA-DEPENDENT MS/MS | TOP 12 MASSES |
| ISOLATION WIDTH | 2.0 |
| RESOLUTION | 17,500 |
| AGC TARGET | 2E5 |
| MAXIMUM INJECTION TIME (ms) | 250 |
| NORMALIZED COLLISION ENERGY (%) | 25 |
| UNDERFILL RATIO (%) | 0.1 |
| CHARGE EXCLUSION | 7, 8 > 8 |
| PEPTIDE MATCH | PREFERRED |
| FIXED FIRST MASS | 100 m/z |
| EXCLUDE ISOTOPE | ON |
| EXCLUSION DURATION(s) | 20 |

Peptides were identified by database searching MS/MS spectra, and the reporter ion ratios (i.e., ratio of 127 label/126 label) were used to calculate fold changes (i.e., localized structural deviations) for each labelled peptide.

Figure 1B:
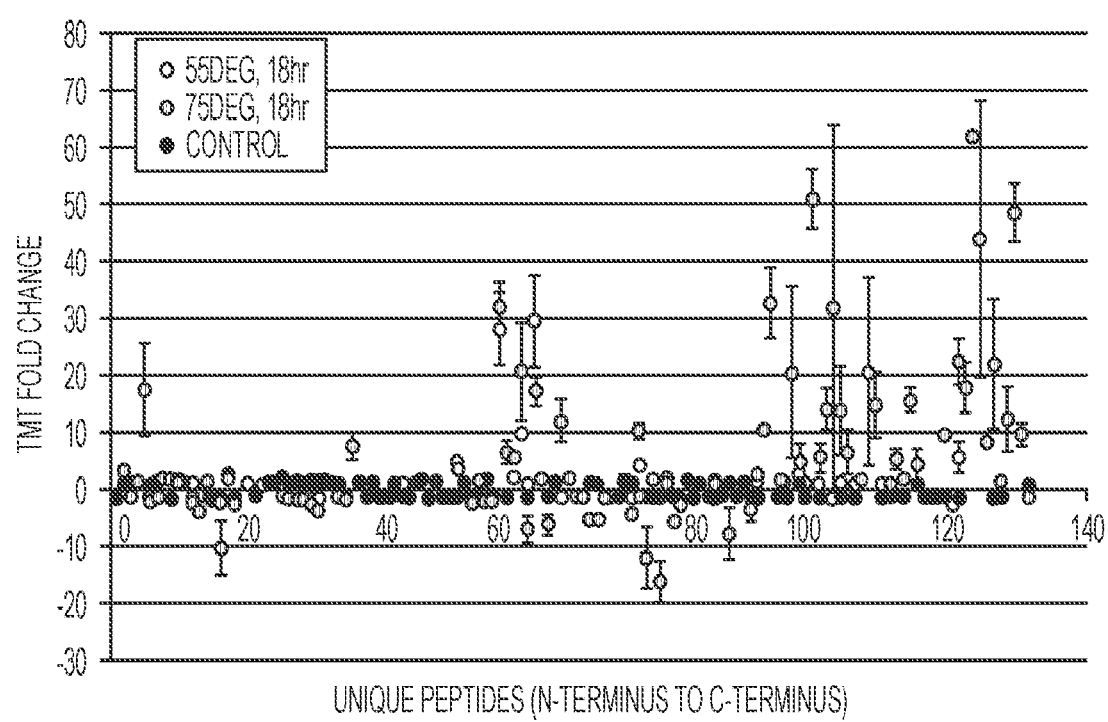
FIG. 1B is a representation of differences of relative levels of labeled peptides from a model Fc fusion protein after exposure to 55 C or 75 C.

FIG. 1A depicts fold changes of labelled peptides relative to sequence position of the model Fc fusion protein for the label-stressed control. FIG. 1B depicts fold changes of labelled peptides relative to sequence position of the model Fc fusion protein for the label-stressed control, the 55° C. mixture, and the 75° C. mixture. As shown in FIG. 1B, the highest fold changes occurred at the C-terminal portion of the Fc fusion protein (i.e., the Fc region of the fusion protein).

Figure 2:
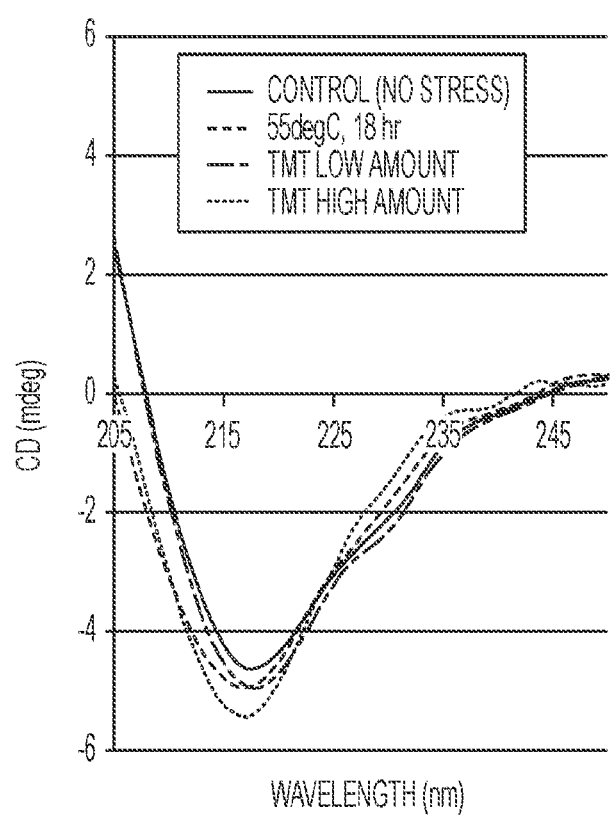
FIG. 2 is a representation of circular dichroism analysis of a model Fc fusion protein labeled with varying amounts of a TMT label or exposed to 55 C.

Different concentrations of isobaric label were used to assess the effect of the isobaric label on higher-order structure. Samples of the model Fc fusion protein were exposed to 55° C. for 18 hours, or were labeled with a low amount (5 µg) of TMT label or with a high amount (200 µg) of TMT label. A control sample of the model Fc fusion protein was not exposed to 55° C. or labeled with the TMT label. The samples were then analyzed by circular dichroism. As shown in FIG. 2, the sample labeled with the high level of TMT label demonstrated the highest level of disorder, indicating that the high level of TMT induced a larger shift in higher-order structure, relative to control.

Figure 3:
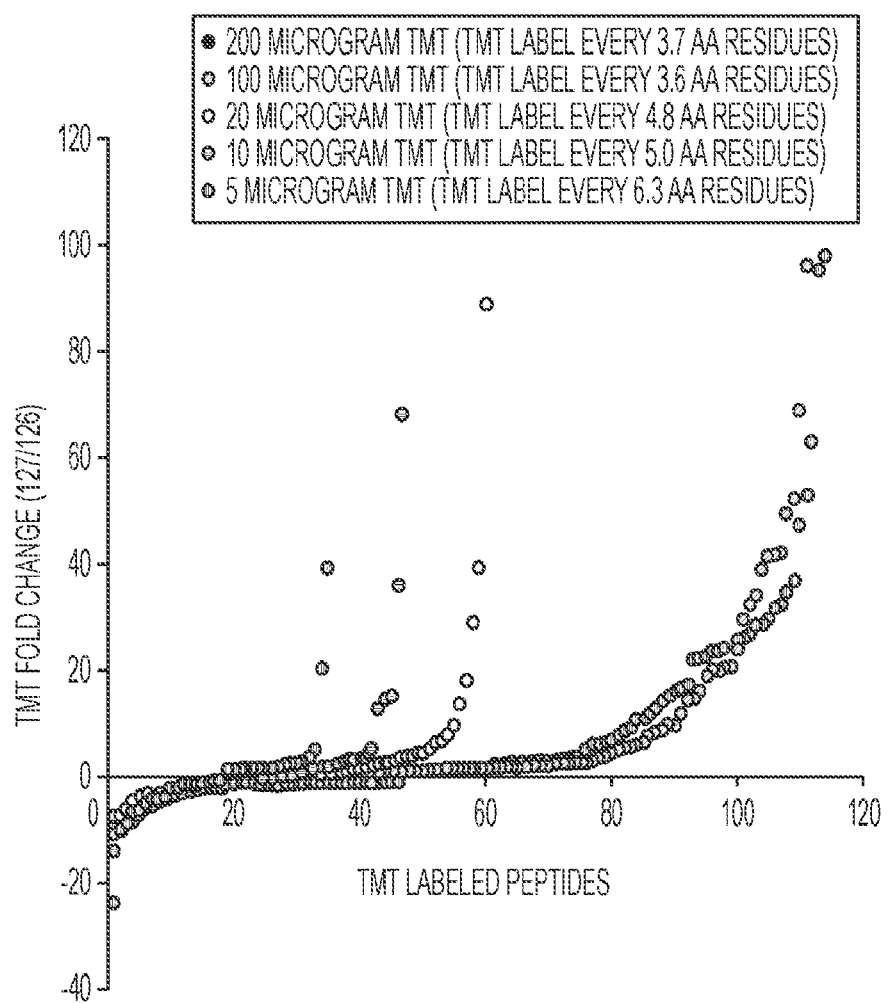
FIG. 3 is a representation of differences of relative levels of labeled peptides from a model Fc fusion protein labeled with different levels of TMT label.

In addition, samples of the model Fc fusion protein were analyzed by labeling with different concentrations of the TMT reagent. Samples were exposed to 75° C. for 18 hours and then labeled with the "127" TMT reagent as described above, but using 5 µg, 10 µg, 20 µg, 100 µg, or 200 µg of the "127" TMT reagent. The 75° C. 127-labeled samples were mixed 1:1 with samples (not subjected to 75° C.) labeled with corresponding concentrations of the "126" TMT reagent. As shown in FIG. 3, the highest level of TMT reagent labeled about every 3.7 amino acid residues, and also resulted in the largest number of peptides with high fold changes (≥2). These results demonstrate that the highest tested level of label (levels which will cause a protein conformation change) resulted in the most sensitive detection of changes to higher-order structure.

Figure 4A:
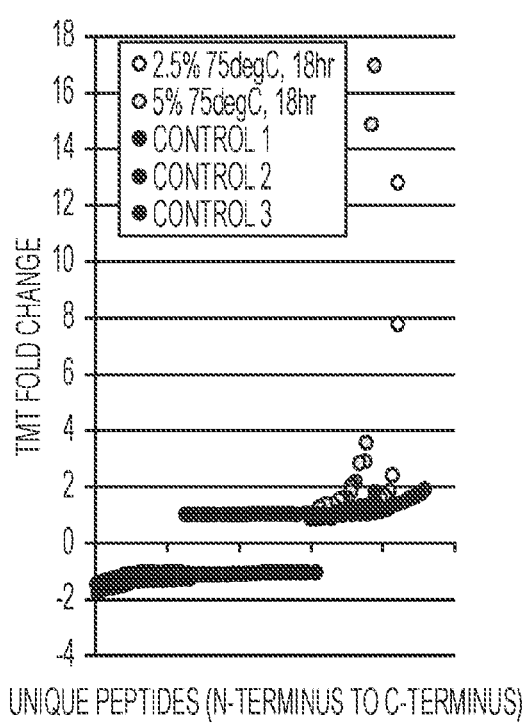
FIG. 4A is representation of differences of relative levels of labeled peptides from a mixture of degraded model Fc fusion protein (2.5% or 5%) and non-degraded model Fc fusion protein.
Figure 4B:
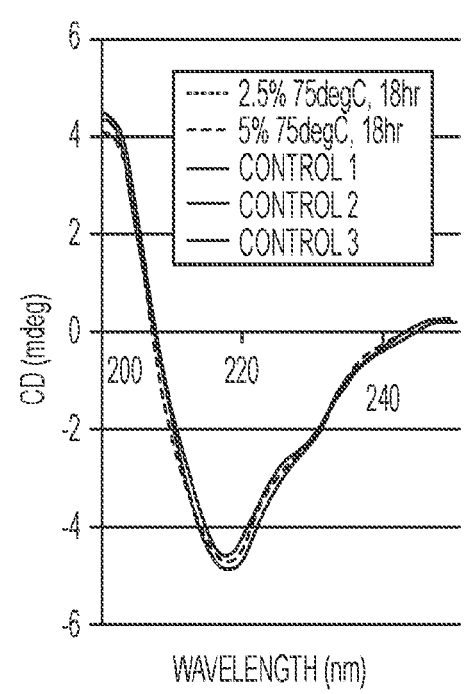
FIG. 4B is a representation of circular dichroism analysis of mixture of degraded model Fc fusion protein (2.5% or 5%) and non-degraded model Fc fusion protein.

Further, the sensitivity of described methods was assessed by degrading the model Fc fusion protein (by exposure to 75° C. for 18 hours) and mixing varying amounts of the degraded Fc fusion protein with non-degraded Fc fusion protein prior to labeling with the "127" TMT reagent. Separately, samples of non-degraded Fc fusion protein were labeled with the "126" TMT reagent, and ratios of 127:126 were analyzed as described above. As shown in FIG. 4A, differences in labeled peptides were detected in samples containing as little as 2.5-5% of degraded (and 95-97.5% non-degraded) model Fc fusion protein. This demonstrates that HOS differences can be detected in samples when less than 2.5% of a protein population is degraded. Further, as shown in FIG. 4B, when the samples were analyzed by circular dichroism, no differences between samples and controls were detected, demonstrating the sensitivity of the described methods.

Example 2: Characterization of a Model Fc Fusion Protein Using a TMT 6Plex Procedure Heat Stressing A model Fc fusion protein ("M1") was diluted to 1 mg/mL in 1×PBS buffer (pH 7.4) prior to stressing. Samples were then properly sealed and heated for 18 hours on a heat block at both 55° C. and 75° C. After the incubations, samples were stored at room temperature. No obvious visible precipitation was observed after either heat-stressing condition.

Protein Labeling

For the TMT sixplex procedure, 126, 127, 128, 129, 130, and 131 TMT vials (Life Technologies, Carlsbad, Calif.)

were allowed to reach room temperature for 30 minutes. Each 0.8 mg TMT vial was reconstituted with 40 µL of acetonitrile, and vortexed for at least one minute. Using a multi-channel pipette, 5 µL of each TMT solution was added to a separate microcentrifuge tube, followed by the addition of 50 µL of controls 1-3 and samples 4-6 (1 µg/µL) to the appropriate TMT aliquot. Reactions were immediately mixed by 10 up-and-down pipette actions, and then incubated for two minutes. After the incubation period, each reaction was simultaneously quenched and denatured by adding 50 µL of 6 M guanidine hydrochloride in 20 mM sodium phosphate/100 mM sodium chloride (pH 7.0) containing 5% hydroxylamine, and mixed by 10 up-and-down pipette actions. All six quenched reactions were equally mixed by adding 16 µL of each sample for a total volume of 96 µL.

Protein Preparation and LC-MS/MS Analysis

Labeled samples were reduced and alkylated by adding 2 µL of 0.5 M Tris (2-carboxyethyl) phosphine hydrochloride (TCEP) solution and incubating for 30 minutes at 37° C., and then adding 2 µL of 1 M iodoacetamide and incubating for one hour in the dark. Using Zeba spin columns, samples were then buffer exchanged into 50 mM ammonium bicarbonate containing 12 mM methionine (final volume of 150 µL), and digested with 2 µg of chymotrypsin (1:25 enzyme to substrate ratio) for one hour in a Barocycler (Pressure Biosciences, South Easton, Mass.) operated at 20,000 psi. The chymotrypsin reaction was quenched with 2% formic acid.

The resulting peptides were analyzed using LC-MS/MS by injecting 2 µg of sample onto a 2.1×50 mm (1.7 µm particle size) AQUITY BEH C18 column (Waters, Milford, Mass.) heated at 50° C. using a Dionex Ultimate 3000 RSLCnano (Santa Clara, Calif.) system. Peptide separation was performed with eluent A consisting of 0.1% formic acid in water and eluent B consisting of 0.1% formic acid in acetonitrile, and a 95 min linear gradient from 4% to 35% eluent B at a flow rate of 50 µL/min.

Data-dependent MS/MS was performed on a Thermo Scientific Q Exactive mass spectrometer (Bremen, Germany) as follows: the first event was the survey positive mass scan (m/z range of 400-2000) followed by HCD events (30% NCE) on the twelve most abundant ions from the first event. Ions were generated using a spray voltage of 3.32 kV, a capillary temperature of 275° C., and an S-Lens RF level of 85. Resolution and AGC was set at 35,000 and 1E6 for survey scans and 17,500 and 2E5 for MS/MS events. A maximum injection time of 250 ms was used for all scans. A dynamic exclusion duration of 20 s was used with a single repeat count. Both full MS and MS/MS spectra were produced from one microscan.

Peptide Identification and Higher Order Structure Quantification

The entire peptide identification and quantitation data analysis workflow described below was fully automated using Proteome Discoverer, version 1.4 (Thermo Scientific, Bremen, Germany). A protein database composed of the sequence of M1 and common protein contaminants was used to search against the experimental MS/MS using both SEQUEST 40 and Byonic 41 within Proteome Discoverer. A mass tolerance of 10 ppm and 0.02 Da were used for precursor and fragment masses, respectively, and up to two missed cleavages were allowed. Carbamidomethyl of cysteine was used as a fixed modification. TMT 6plex was set as a variable modification on lysine, serine, threonine, and the N-terminus; deamidation of asparagine and oxidation of methionine were also set as variable modifications. A database consisting of the top 13 glycans was used by Byonic for identifying glcyopeptides. Byonic "Wildcard" (Bern et al., Curr. Protoc. Bioinformatics, Chapter 13, Unit 1320 (2012)) searches with a delta mass range of −130 to +230 Daltons were also employed to cover a wide array of potential sequence modifications and substitutions.

Fold changes were calculated by Proteome Discoverer using an integration tolerance of 20 ppm, isotopic quantitative value correction, and a maximum allowed fold change of 100. MS/MS spectra that yielded fold changes greater than two were manually verified by assessing TMT channel interference and MS/MS patterns. Decimal fold changes were converted using −1 divided by the decimal to give equal weight between decimal and non-decimal fold changes, and for better visualization of areas in the protein that have become more protected after stressing. Three replicates were prepared and analyzed at each condition (stressed or unstressed) for repeatability experiments, and error bars represent standard deviations of the fold changes.

Results

Assessing Local HOS Changes and Repeatability

Figure 5A:
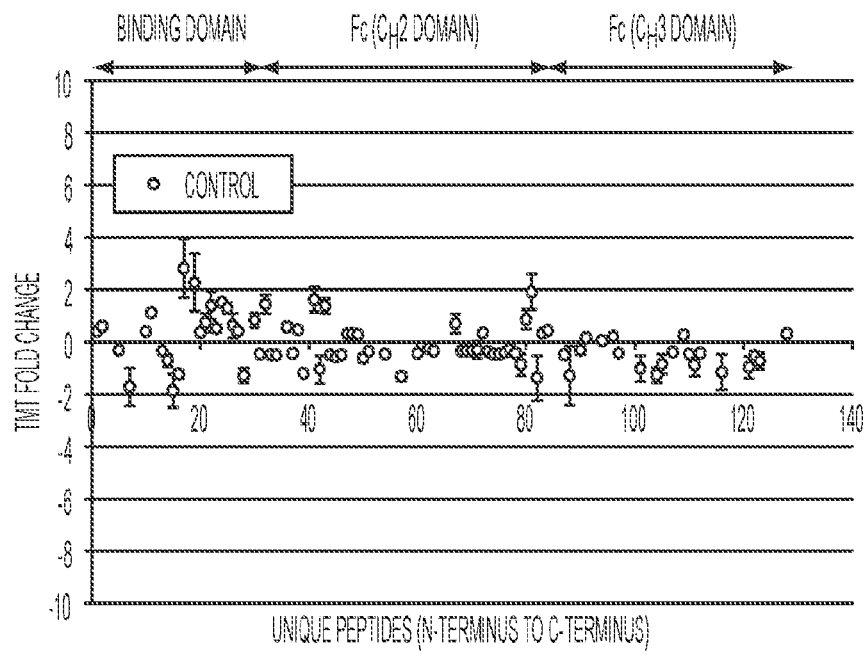
FIG. 5A is a representation of differences of relative levels of TMT sixplex labeled peptides from a model Fc fusion protein.

TMT sixplex was used to characterize the protein locations in M1 where HOS changes were occurring for both heat-stressing conditions (75° C. and 55° C. for 18 hours), and to more thoroughly assess the repeatability of the methodology. FIG. 5A depicts a plot of fold change versus unique TMT peptides (arranged from N- to C-terminus) from TMT sixplex labeling for a control run (all six TMT channels were used to label unstressed M1). The fold changes are from the average of the 129/126, 130/127, and 131/128 reporter ions (decimal fold changes were converted to negative values before averaging). The control run showed fold changes of one or lower to be dominant, but increased to around two due to experimental error. The replicate measurements were also highly reproducible as shown by the error bars.

Figure 5B:
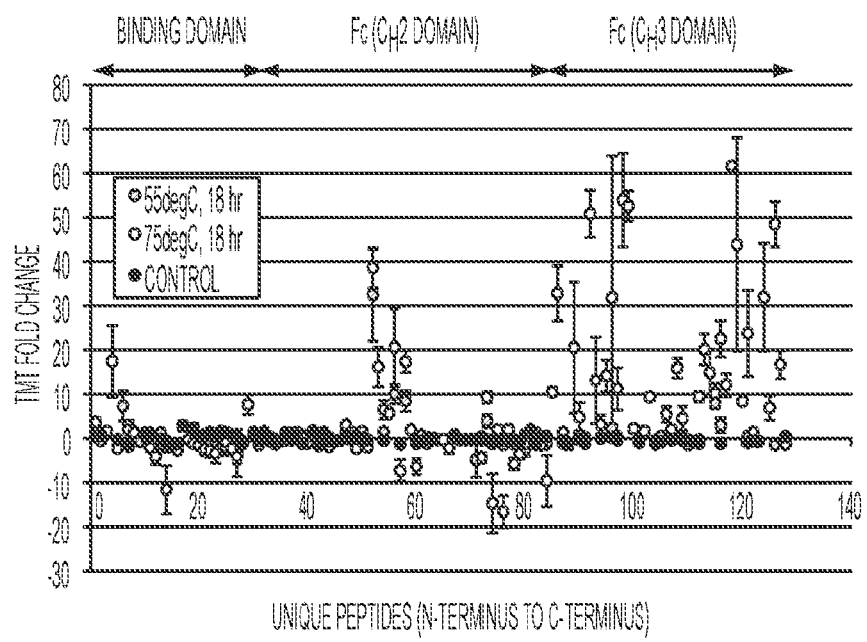
FIG. 5B is a representation of differences of relative levels of TMT sixplex labeled peptides from a model Fc fusion protein after exposure to 55 C or 75 C.
Figure 6:
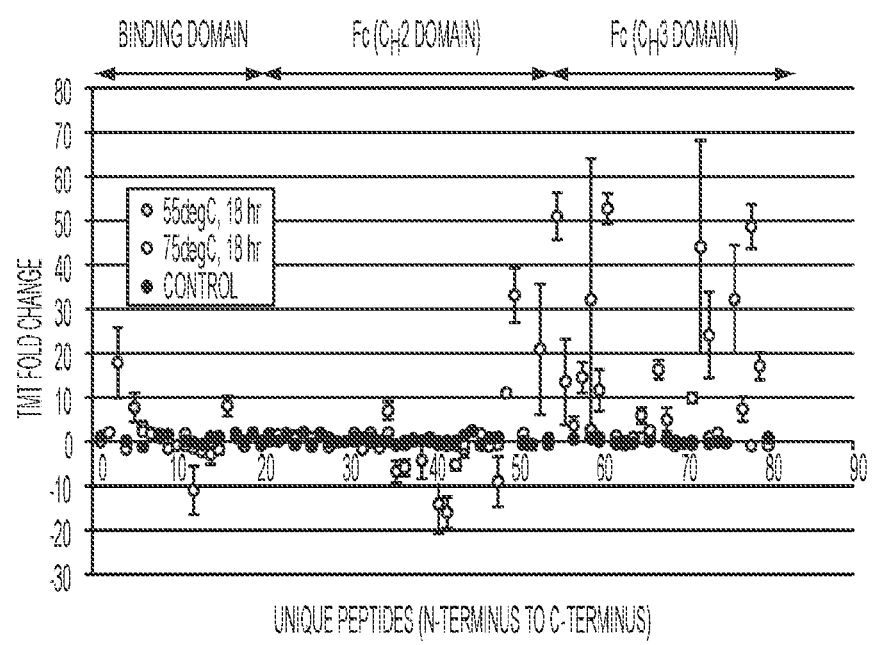
FIG. 6 is a representation of the data of FIG. 5B with all oxidized, deamidated, and glycosylated peptides filtered out.

FIG. 5B depicts the same control analysis along with TMT sixplex labeling of the two different heat-stressing conditions (55° C. for 18 hours or 75° C. for 18 hours versus unstressed M1). Three replicates were performed for each condition (e.g., TMT 126, 127, and 128 was reacted with three separate unstressed aliquots and TMT 129, 130, and 131 was reacted with three separate aliquots from the same heat-stressing condition). Assessment of HOS changes can be more straightforward from TMT labeled peptides that do not contain post-translational modifications (PTMs) because HOS change can be difficult to separate from the degree of PTM change. Therefore, the data from FIG. 5B, with all oxidized, deamidated, and glycosylated peptides filtered out, can also be seen in FIG. 6.

M1 has two melting transitions as confirmed by differential scanning calorimetry (data not shown), one near 55° C. and one slightly over 75° C., was therefore the main reason these temperatures were selected for the heat-stressing samples in this study. Based on previous reports, the first transition (~55° C.) is likely the unfolding of both the protein binding and Fc CH2 domains, and the second transition (~75° C.) is likely the unfolding of the Fc CH3 domain (Liu et al., J. Immunol. Lett. 106:144-153 (2006); Demarest et al., Curr. Opin. Drug Discov. Devel. 11:675-687 (2008); Ghirlando et al., Immunol. Lett. 68:47-52 (1999); Fast et al., Biochemistry 48:11724-11736 (2009)). Interestingly, while the 75° C. heat-stressed sample yielded regions of high fold change throughout the protein (due to the high level of stress), two general regions in the Fc CH3 domain yielded the most dramatic differences. Many of these peptides with very high fold changes also had a considerable amount of associated error, possibly because the TMT reporter ions from the unstressed M1 sample were near the MS detection limit, and the TMT channels that were not detected were replaced with minimum spectral intensities. Since this sample was highly stressed, many conformations may be present and certain unfolded sections may be highly flexible, both of which can increase error compared to what was observed for the Control (FIG. 5A). Conversely, the highest fold changes for the 55° C. heat-stressed sample were located in the Fc CH2 domain. The fold changes for the 55° C. sample, however, were from labeled peptides that were also deamidated. While deamidation can cause HOS changes via the addition of negative charge (Wright et al., Crit. Rev. Biochem. Mol. Biol. 1991, 26:1-52; Takata et al., J. Protein Sci. 2008, 17:1565-1575; Huang et al., Anal. Chem. 2005, 77:1432-1439; Luo et al., J. Biol. Chem. 2011, 286:25134-25144; Robinson et al., Proc. Natl. Acad. Sci. U.S.A 2001, 98:12409-12413; Kosky et al., Protein Sci. 1999, 8:2519-2523; Geiger et al., J. Biol. Chem. 1987, 262:785-794; Liu et al., Biologicals 2009, 37:313-322; Liu et al., J. Immunol. Lett. 2006, 106:144-153) it may be difficult to separate the fold change contribution of HOS versus PTM change for the results herein.

There are also areas of the protein in the 75° C. heat-stressed sample that have substantial negative fold changes (i.e., regions that have become more protected in the heat-stressed versus the unstressed sample). Although it is possible that these regions are simply areas where sections of amino acids have become buried in the structure, the more likely cause of the negative fold changes are from sites of aggregation, since the areas of the protein affected by the heat-stressing are expected to be more unfolded in general (less buried).

Simultaneous Quantitation of PTMs, Site-Specific Glycosylation, and Potentially Unforeseen Sequence Modifications The analytical workflow described herein can also be used to simultaneously and automatically quantify other product attributes such as PTMs and site-specific glycosylation, in addition to localized HOS. Deamidation, glycosylation, and oxidation were specifically searched for and quantified using the automated data analysis workflow, as these PTMs are often the most common and important modifications to therapeutic proteins (Liu et al., MAbs 2014, 6:1145-1154) and are routinely monitored during biologics development.

25, 21, and 7 quantifiable unique TMT labeled peptides (i.e., ones that had fold changes) were detected that were deamidated, glycosylated, and oxidized, respectively, from the combined data of the control and two stressed conditions presented in FIG. 5. These peptides covered 16 unique PTM sites. As expected, the heat-stressed samples showed substantially higher degrees of deamidation compared to the control samples (up to 62-fold change)—especially for the "hot spot" PTMs that tend to increase at the highest rates. Oxidation was often elevated as well for the stressed samples, but more moderately (up to 4-fold change). Interestingly, many of the areas in the protein with high fold changes for deamidation also had high fold changes associated with HOS unfolding; however, it is difficult to decipher whether the deamidation induced conformation denaturation or vice versa.

A large percentage of quality MS/MS spectra with peptide-like fragmentation patterns do not get matched to peptides in data-dependent LC-MS/MS experiments (Chick et al., Nat. Biotechnol. 2015, 33:743-749). Many of the unidentified spectra are actually peptides with unpredictable sequence modifications (Chick et al., Nat. Biotechnol. 2015, 33:743-749). Error tolerant searches have therefore sought to identify many of these MS/MS spectra by modifying all amino acid residues by a specified mass delta (Bern et al., Curr. Protoc. Bioinformatics 2012, Chapter 13, Unit 1320; Chick et al., Nat. Biotechnol. 2015, 33:743-749; Creasy et al., Proteomics 2002, 2:1426-1434; Yang et al., MAbs 2010, 2:285-298). One of the biggest drawbacks of error tolerant searches, however, is the high number of false positive identifications. Therefore, deciphering true positive from these identifications can be exceedingly challenging and time consuming. The high false positive rate comes from the large search space created by the error tolerant searches, and thus MS/MS spectra collected with data-dependent peak picking errors and poor fragmentation patterns end up as peptide identifications that are incorrect with unlikely modifications.

Figure 7A:
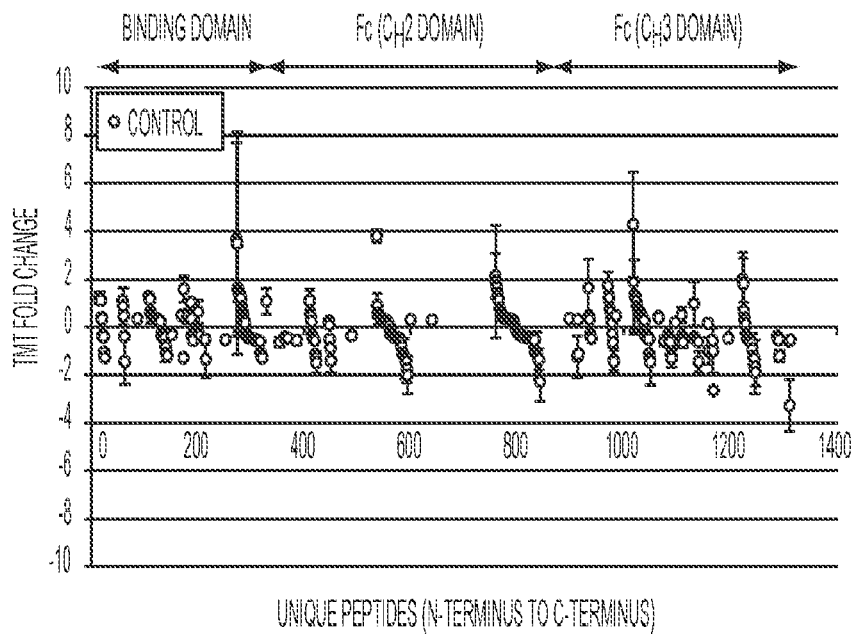
FIG. 7A is a representation of differences of relative levels of labeled peptides from a model Fc fusion protein using "wildcard"/error tolerant searches in an automated data analysis workflow.
Figure 7B:
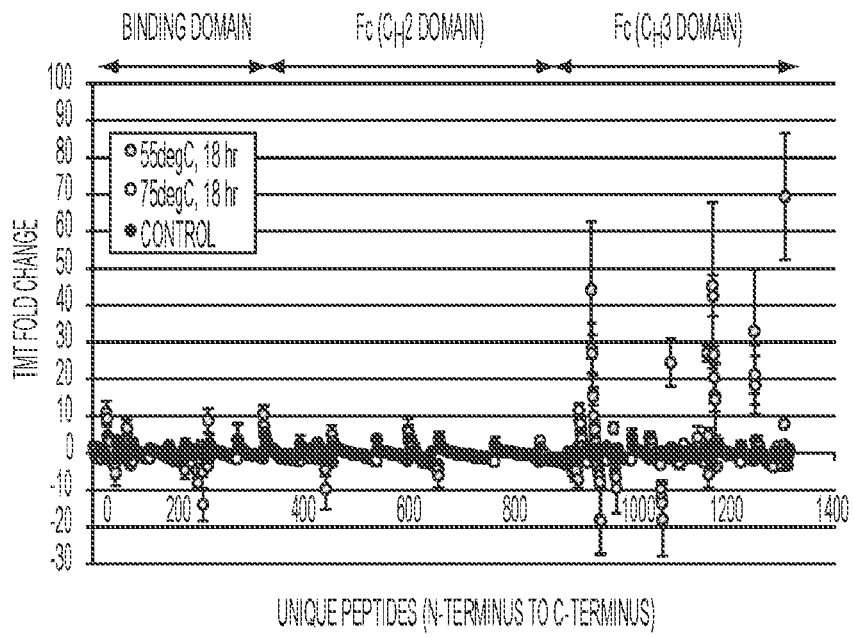
FIG. 7B is a representation of differences of relative levels of labeled peptides from a model Fc fusion protein after exposure to 55 C or 75 C using "wildcard"/error tolerant searches in an automated data analysis workflow.

To assess the applicability of error tolerant searches to the methodology presented herein, the data presented in FIG. 5 were mined for unpredicted sequence modifications by directly incorporating Byonic "wildcard" (Bern et al., Curr. Protoc. Bioinformatics 2012, Chapter 13, Unit 1320) error tolerant searches into the automated data analysis workflow. An amino acid modification range of −130 to +230 Daltons was used to cover unpredicted TMT modifications, an extensively wide array of PTMs, and other potential sequence modifications. The wildcard output from the LC-MS/MS data originally presented in FIG. 5 can be seen in FIG. 7; only TMT labeled peptides identified from the wildcard search that had sequence modifications and yielded fold change measurements are shown. The wildcard search generated 1,316 unique and modified TMT peptides, which is substantially higher than the 128 unique TMT peptides originally identified in FIG. 5 (no wildcard search). The error in the fold change measurements for the control (see FIG. 7A) was slightly more erroneous as compared to FIG. 5A (a fold change cut-off of 4 instead of 2 would be utilized) due to peptide identifications that were produced from poor MS/MS spectra with interfering ions near the TMT reporter ions. However, the principal advantage of combining error tolerant searches with the TMT workflow for biotherapeutic comparisons is that only peptide hits with high fold changes would need to be verified. All other peptides with low fold changes would be confirmed as equivalent between the samples regardless of whether the hit was a true positive or false positive. As seen in FIG. 7B, this type of filtering would cut out a tremendous amount of data that would need verification, making error tolerant analysis significantly easier.

Example 3: Characterization of a Model Antibody

The assay described in Example 1 was also demonstrated to be capable of assessing higher-order structure of a model antibody. A label-stressed control mixture was first created. Antibody samples were diluted in an amine-free triethyl ammonium bicarbonate buffer at pH 8 with no denaturant. Two aliquots of the antibody were exposed to room temperature for 18 hours. One aliquot was labelled with 100 µg "127" TMT reagent for 2 minutes, and one aliquot was labelled with 100 µg "126" TMT reagent for 2 minutes. The 126-labelled aliquot was mixed at 1:1 ratio with the 127-labelled aliquot after each reaction was completed to obtain a label-stressed control mixture.

Heat-stressed samples were produced by first diluting antibody samples in an amine-free triethyl ammonium bicarbonate buffer at pH 8 with no denaturant. Antibody samples were analyzed under two heat-stressed conditions. A first sample was exposed to 40° C. for 18 hours, and a second sample was exposed to 55° C. for 18 hours. The samples were then labelled with the "127" TMT reagent at specified reaction times.

Separately, samples of antibody were exposed to room temperature for 18 hours and labelled with the "126" TMT reagent at the same specified reaction times used for the 40° C. and 55° C. samples. The 40° C. and 55° C. 127-labelled samples were mixed 1:1 with the label-stressed (i.e., 126-labelled) samples after each reaction was completed to produce a "40° C. mixture" and a "55° C. sample", respectively.

The label-stressed control mixture, the 40° C. mixture, and the 55° C. mixture were then denatured, reduced, alkylated, and enzymatically digested with chymotrypsin. The resulting peptides from each mixture were then analyzed by LCMS/MS using the parameters described in Example 1. Peptides were identified by database searching MS/MS spectra, and the reporter ion ratios (i.e., ratio of 127 label/126 label) were used to calculate fold changes (i.e., localized structural deviations) for each labelled peptide.

Table 1 lists peptides that were detected by the detectable reporter ions, and the respective associated fold changes (i.e., ratio of 127 label:126 label). Within the listed peptides, the lower case "m" represents methionine oxidation. the lower case "k" signifies TMT reagent modification of lysine, lower case "s" represents TMT reagent modification of serine, and lower case "e" and "d" denotes the TMT reagent has reacted with the protein N-terminus. As seen in the first column ("Label Control Mix"), the label-stressed control mixture did not exhibit significant fold changes. However, as shown in the second and third columns (labeled "40° C. mixture" and "55° C. mixture", respectively), the heat-stressed samples exhibited a significant increase in peptides.

TABLE 1

| NEG. CONTROL MIX | FOLD CHANGE (127/126) | 40 C MIXTURE | FOLD CHANGE (127/126) |
|---|---|---|---|
| dlQmTQSPSSL | 1.6 | mISRTPEVTcVVVDVSHEDPEVkF | 4.2 |
| sKADYEkHVY | 1.4 | dlQmTQSPSSL | 3.5 |
| nSGHIDYADSVEGRF | 1.3 | NsGHIDYADSVEGRF | 2.1 |
| sSPVTKsF | 1.3 | SGsGSGTDF | 2.0 |
| kGQPREPQVY | 1.3 | kGQPREPQVY | 1.8 |
| SLSSVVTVPSSsLGTQTY | 1.3 | SLSSVVTVPSsSL | 1.7 |
| EkHkVY | 1.2 | sKADYEkGkVY | 1.7 |
| kVDNALQSGNSQESVTEQDSKDsTY | 1.2 | KVDNALQSGNSQESVTEQDSKDSTY | 1.7 |
| NGkEY | 1.2 | QQKPGkAPKLL | 1.7 |
| sTASSL | 1.1 | kTTPPVLDSDGSFF | 1.7 |
| dlQMTQSPSSL | 1.1 | gQGTkVEIKRTVAAPSVF | 1.7 |
| gQGTKVEIkRTVAAPSVF | 1.1 | LFPPKPkDTL | 1.6 |
| VkDYFPEPVTVSW | 1.1 | GQGTkVEIKRTVAAPSVF | 1.6 |
| LsTASSL | 1.1 | VTVSSASTkGPSVFPL | 1.6 |
| kTTPPVLDSDGSFF | 1.1 | SLSSVVTVPSSsLGTQTY | 1.6 |
| kSGTASWcLL | 1.1 | kVDNALQSGNSQESVTEQDSKDsTY | 1.6 |
| TLPPSRDELTkNQVSL | 1.1 | TLSkADY | 1.6 |
| eVQLVESGGGLVQPGRSL | 1.1 | YcAkVSY | 1.6 |
| TISRDNAkNSL | 1.0 | TISRDNAkNSL | 1.5 |
| SGsGSGTDF | 1.0 | VRQAPGkGLEW | 1.5 |
| MISRTPEVTcVVVDVSHEDPEVkF | 1.0 | kSGTASVVcL | 1.5 |
| VTVSSASTkGPSVF | 1.0 | HQDWLNGkEY | 1.5 |
| HQDWLNGkEY | 1.0 | YPREAkVQW | 1.6 |
| mISRTPEVTcVVVDVSHEDPEVkF | 1.0 | LNGkEY | 1.5 |
| SLSSVVTVPSSsL | 1.0 | TISRDNAkNSLY | 1.4 |
| QQkPGkAPKLL | 1.0 | AcEVTHQGLSSPVTKsF | 1.4 |
| TVDkSRWQQGNVF | 1.0 | QQkPGkAPKLL | 1.4 |
| dYWGQGTL | 1.0 | TVDKsRWQQGNVF | 1.4 |
| QSGNSQESVTEQDSkDSTY | 1.0 | VkDYFPEPVTVSW | 1.4 |
| kTTPPVLDSDGSF | 1.0 | cAkVSYL | 1.4 |
| VDGVEVHNAkTkPREEQY | 1.0 | kSGTASVVcLL | 1.4 |
| VRQAPGkGLEW | 1.0 | dlQMTQSPsSL | 1.4 |
| TISRDNAkNSLY | 1.0 | eVQLVESGGGLVQPGRSL | 1.4 |
| TLSkADY | 1.0 | SLSPGk | 1.4 |
| AcEVTHQGLSSPVTkSF | 0.9 | kTTPPVLDSDGSF | 1.4 |
| ISRTPEVTcVVVDVSHEDPEVkF | 0.9 | sKADYEKHkVY | 1.4 |
| YPREAkVQW | 0.9 | TLPPSRDELTkNQVSL | 1.4 |
| VTVSSAsTKGPSVFPL | 0.9 | dlQMTQSPSSL | 1.4 |
| eVQLVESGGGL | 0.9 | eVQLVESGGGL | 1.4 |
| kVDNAL | 0.9 | cAKVSY | 1.4 |
| kSGTASVVcL | 0.9 | TkNQVSL | 1.4 |
| GQGTKVEIkRTVAAPSVF | 0.9 | GQGTLVTVSSASTkGPSVF | 1.4 |
| kVDNALQSGNSQESVTEQDSKDSTY | 0.9 | QSGNSQESVTEQDSkDSTY | 1.4 |
| GQGTLVTVSSASTkGPSVF | 0.8 | VTVSSASTkGPSVF | 1.4 |
| QQkPGkAPKLL | 0.8 | MISRTPEVTcVVVDVSHEDPEVkF | 1.3 |
| LFPPKPkDTL | 0.7 | ISRTPEVTcVVVDVSHEDPEVkF | 1.3 |
| TkNQVSL | 0.7 | LsTASSL | 1.0 |
| sKADYEKHkVY | 0.5 | | |

TABLE 1-continued

| 56 C MIXTURE | FOLD CHANGE (127/126) |
|---|---|
| eVQLVEsGGGL | 14.3 |
| dlQMTQSPSsL | 6.2 |
| SLSSVVTVPSsSL | 5.9 |
| mISRTPEVTcVVVDVSHEDPEVkF | 3.4 |
| dlQMTQSPSSL | 3.0 |
| QQkPGkAPkLL | 2.8 |
| cAkVSYL | 2.5 |
| sSPVTKsF | 2.5 |
| YcAkVSY | 2.4 |
| kGQPREPQVY | 2.4 |
| kVDNALQSGNSQESVTEQDSKDSTY | 2.3 |
| gQGTKVElkRTVAAPSVF | 2.1 |
| EVQLVEsGGGL | 2.0 |
| VkDYFPEPVTVSW | 2.0 |
| NsGHIDYADSVEGRF | 1.8 |
| TkNQVSL | 1.8 |
| eVQLVESGGGLVQPGRSL | 1.7 |
| sKADYEkHkVY | 1.7 |
| kTTPPVLDSDGSFF | 1.6 |
| TLPPSRDELTkNQVSL | 1.6 |
| dYVVGQGTL | 1.5 |
| TVDKsRWQQGNVF | 1.5 |
| EkHkVY | 1.5 |
| QSGNSQESVTEQDSkDSTY | 1.5 |
| kTTPPVLDSDGSF | 1.5 |
| GQGTLVTVSSASTKGPsVF | 1.5 |
| SLSPGk | 1.4 |
| VTVSSASTkGPSVF | 1.4 |
| TLSkADY | 1.3 |
| KsGTASVVcLL | 1.3 |
| sTASSL | 1.3 |
| TISRDNAkNSLY | 1.3 |
| QQkPGkAPKLL | 1.3 |
| AcEVTHQGLSSPVTkSF | 1.2 |
| kSGTASVVcL | 1.2 |
| LSTASsL | 1.2 |
| SSPVTkSF | 1.1 |
| VRQAPGkGLEW | 1.1 |
| MISRTPEVTcVVVDVSHEDPEVkF | 1.1 |
| HQDWLNGkEY | 1.1 |
| TISRDNAkNSL | 1.1 |
| ISRTPEVTcVVVDVSHEDPEVkF | 1.0 |
| GQGTKVElkRTVAAPSVF | 1.0 |
| kVDNALQSGNSQESVTEQDSKDSTY | 1.0 |
| LFPPKPkDTL | 0.8 |
| SkADYEKHkVY | 0.8 |

Example 4: Manufacture of a Biosimilar Fc Fusion Protein

A batch of a test Fc fusion protein is produced as a drug substance. A sample of the test Fc fusion protein in a first state is exposed to a stressor to obtain a labeled test Fc fusion protein in a second state. Mass spectrometry is used to obtain a test MS signal of the labeled test Fc fusion protein. The test MS signal is compared to a target MS signal for a target Fc fusion protein drug product (approved under a primary approval process) which has been exposed to the same stressor. The variability between the test MS signal and the target MS signal does not exceed the variability of MS signals determined for two distinct batches of the target Fc fusion protein assessed using the same MS and stressor. The batch of test Fc fusion protein is processed as drug product.

Example 5: Manufacture of a Biosimilar Antibody

A batch of a test antibody is produced as a drug substance. A sample of the test antibody in a first state is exposed to a stressor to obtain a labeled test antibody in a second state. Mass spectrometry is used to obtain a test MS signal of the labeled test antibody. The test MS signal is compared to a target MS signal for a target antibody drug product (approved under a primary approval process) which has been exposed to the same stressor. The variability between the test MS signal and the target MS signal does not exceed the variability of MS signals determined for two distinct batches of the target antibody assessed using the same MS and stressor. The batch of test antibody is processed as drug product.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of manufacture, comprising:
producing a batch of test protein drug substance;
exposing a sample of the test protein in a first state to a stressor to obtain a labeled test protein in a second state, wherein the stressor comprises a first level of a first isobaric label that alters a higher-order structure of the test protein;
using mass spectrometry (MS) to obtain a test MS signal of the labeled test protein;
comparing the test MS signal to a target MS signal for a target protein drug product exposed to a first level of a second isobaric label, wherein the first level of the second isobaric label is the same as the first level of the first isobaric label, and wherein the target protein is approved under a primary approval process; and
processing the batch of the test protein drug substance as drug product if the test MS signal and the target MS signal are tolerable; or
taking an alternative action if the test MS signal and the target MS signal are not tolerable.

2. The method of claim 1, wherein using MS comprises digesting the labeled test protein to produce a plurality of labeled test peptides.

3. The method of claim 1, the test MS signal and the target MS signal are tolerable if they meet a predetermined value.

4. The method of claim 1, wherein the test MS signal and the target MS signal are tolerable if a peptide level obtained from the test MS signal and a corresponding peptide level obtained from the target MS signal differ by no more than 10%.

5. The method of claim 1, wherein the first state is a native state and the second state is a non-native state.

6. The method of claim 1, wherein the alternative action comprises one or more of disposing of the test protein, classifying for disposal the test protein, labeling the test protein for disposal, and reprocessing the test protein.

7. The method of claim 1, further comprising producing a representation of the comparison of the test MS signal and the target MS signal.

8. The method of claim 1, wherein the target protein has an amino acid sequence that is 100% identical to the test protein, and wherein the target protein is approved under a BLA.

9. The method of claim 1, wherein the test MS signal comprises a plurality of signals from an MS spectrum of the test protein.

10. The method of claim 1, further comprising exposing a sample of the target protein in a first state to a stressor comprising a first level of the second isobaric label to obtain a labeled target protein in a second state, wherein the first level of the second isobaric label is the same as the first level of the first isobaric label.

11. The method of claim 1, further comprising using MS to obtain a target MS signal of a labeled target protein.

12. The method of claim 1, further comprising using MS to obtain a target MS signal of the labeled target protein, wherein using MS comprises digesting the labeled target protein to produce a plurality of labeled target peptides.

13. The method of claim 1, wherein the test protein is an Fc fusion protein or an antibody.

14. The method of claim 1, wherein the processing step comprises one or more of: formulating the test protein; combining the test protein with a second component, e.g., an excipient or buffer; changing the concentration of the test protein in the preparation; lyophilizing the test protein; combining a first and second aliquot of the test protein to provide a third, larger, aliquot; dividing the test protein into smaller aliquots; disposing the test protein into a container, e.g., a gas or liquid tight container; packaging the test protein; associating a container comprising the test protein with a label (e.g., labeling); shipping or moving the test protein to a different location.

15. The method of claim 1, further comprising:
exposing a second sample of the test protein in the first state to a second level of a third isobaric label to obtain labeled test protein in a third state;
using MS to obtain a second test MS signal of the labeled test protein in the third state;
comparing the second test MS signal to a second target MS signal for the target protein drug product exposed to a second level of a fourth isobaric label, wherein the second level of the fourth isobaric label is the same as the second level of the third isobaric label; and
processing the batch of the test protein drug substance as drug product if the second test MS signal and the second target MS signal are tolerable; or
taking an alternative action if the second test MS signal and the second target MS signal are not tolerable.

16. The method of claim 1, wherein the test protein is a glycoprotein.

17. The method of claim 1, wherein the isobaric labels comprise TMT, iTRAQ or ICAT labels.

18. The method of claim 1, wherein the first isobaric label and the second isobaric label are the same.

19. The method of claim 1, wherein the first isobaric label and the second isobaric label have the same chemical structure but different mass.

20. The method of claim 15, wherein the first isobaric label and the third isobaric label are the same, and wherein the second isobaric label and the fourth isobaric label are the same.

21. The method of claim 15, wherein the first isobaric label and the third isobaric label have the same chemical structure but different mass, and wherein the second isobaric label and the fourth isobaric label have the same chemical structure but different mass.

* * * * *